(12) United States Patent
Koeberl

(10) Patent No.: US 8,679,478 B2
(45) Date of Patent: Mar. 25, 2014

(54) METHODS OF LYSOSOMAL STORAGE DISEASE THERAPY

(75) Inventor: Dwight D. Koeberl, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 13/253,005

(22) Filed: Oct. 4, 2011

(65) Prior Publication Data
US 2012/0082653 A1 Apr. 5, 2012

Related U.S. Application Data

(60) Provisional application No. 61/420,828, filed on Dec. 8, 2010, provisional application No. 61/389,494, filed on Oct. 4, 2010.

(51) Int. Cl.
*A61K 38/43* (2006.01)

(52) U.S. Cl.
USPC .................................................. 424/94.1

(58) Field of Classification Search
USPC .................................................. 424/94.1
See application file for complete search history.

(56) References Cited

U.S. PATENT DOCUMENTS

| | | | |
|---|---|---|---|
| 5,236,838 A | 8/1993 | Rasmussen | |
| 5,382,524 A | 1/1995 | Desnick | |
| 5,401,650 A | 3/1995 | Desnick | |
| 5,686,240 A | 11/1997 | Schuchman et al. | |
| 5,879,680 A | 3/1999 | Ginns | |
| 6,946,126 B2 * | 9/2005 | Amalfitano et al. | 424/93.2 |
| 2004/0029779 A1 * | 2/2004 | Zhu et al. | 514/3 |

FOREIGN PATENT DOCUMENTS

| | | |
|---|---|---|
| WO | WO 93/10244 | 5/1993 |
| WO | WO 00/12740 | 3/2000 |

OTHER PUBLICATIONS

Hawkes et al. The insulin-like growth factor-II/mannose-6-phosphate receptor: structure, distribution and function in the central nervous system. Brain Res Rev 44:117-140, Mar. 2004.*
Amalfitano et al., "Systemic correction of the muscle disorder glycogen storage disease type II after hepatic targeting of a modified adenovirus vector encoding human acid-alpha-glucosidase," *Proc. Natl. Acad. Sci. USA*, 1999, 96(16):8861-8866.
Amalfitano et al., "Recombinant human acid alpha-glucosidase enzyme therapy for infantile glycogen storage disease type II: results of a phase I/II clinical trial." *Genet. Med.*, 2001, 3(2):132-138.
Angelini et al., "Comparative study of acid maltase deficiency. Biochemical differences between infantile, childhood, and adult types,"*Arch. Neural.*,1972,26:344-349.
Angelini et al., "Italian multicentric trials in Duchenne dystrophy," *Ital. J. Neurol. Sci*, 1984, 4:137-142.
Angelini et al., "An open trial of albuterol and branched chain aminoacids in adult acid maltase deficiency," *Neurology*, 1998, 50:A369.
Angelini et al., "Adult Acid Maltase Deficiency: an Open Trial with Albuterol and Branched—Chain Aminoacids," *Basic Appl. Myol.*, 2004,14(2):71-78.
Awede et al., "Role of IGF-I and IGFBPs in the changes of mass and phenotype induced in rat soleus muscle by clenbuterol," *Am. J. Physiol. Endocrinol. Metab.*, 2002, 282:E31-37.
Blanz et al., "Reversal of peripheral and central neural storage and ataxia after recombinant enzyme replacement therapy in alpha-mannosidosis mice," *Hum. Mol. Genet.*, 2008, 17:3437-45.
Braulke et al., "Regulation of the mannose 6-phosphate/IGF II receptor expression at the cell surface by mannose 6-phosphate, insulin like growth factors and epidermal growth factor," *EMBO J.*, 1989, 8:681-686.
Braulke et al., "Insulin-like growth factors I and II stimulate endocytosis but do not affect sorting of lysosomal enzymes in human fibroblasts," *J. Biol. Chem.*,1990, 265:6650-6655.
Cardone et al., "Abnormal mannose-6-phosphate receptor trafficking impairs recombinant alpha-glucosidase uptake in Pompe disease fibroblasts," *Pathogenetics*, 2008, 1:6.
Case et al., "Improvement with ongoing Enzyme Replacement Therapy in advanced late-onset Pompe disease: a case study," *Mol. Genet. Metab.*, 2008, 95:233-235.
Cresawn et al., "Impact of humoral immune response on distribution and efficacy of recombinant adeno-associated virus-derived acid alpha-glucosidase in a model of glycogen storage disease type II, *Hum. Gene Ther.*, 2005,16:68-80.
Daly et al., "Neonatal intramuscular injection with recombinant adeno-associated virus results in prolonged beta-glucuronidase expression in situ and correction of liver pathology in mucopolysaccharidosis type VII mice," *Hum. Gene. Ther.*,1999, 10(1):85-94.
Daly et al., "Prevention of systemic clinical disease in MPS VII mice following AAV-mediated neonatal gene transfer," *Gene. Ther.*, 2001, 8(17):1291-1298.
Damke et al., "Simultaneous redistribution of mannose 6-phosphate and transferrin receptors by insulin-like growth factors and phorbol ester," *Biochem. J.*, 1992, 281:225-229.
Desnick, "Enzyme replacement and enhancement therapies for lysosomal diseases," *J. Inherit. Metab. Dis.*, 2004, 27:385-410.
El-Shewy et al., "Insulin-like growth factor-2/mannose-6 phosphate receptors," *Vitamins and Hormones*, 2009, 80:667-697.
Franco et al., "Evasion of immune responses to introduced human acid alpha-glucosidase by liver-restricted expression in glycogen storage disease type II," *Mol. Ther.*, 2005, 12:876-884.
Fuller et al., "Isolation and characterisation of a recombinant, precursor form of lysosomal acid alpha-glucosidase," *Eur. J. Biochem.* ,1995, 234(3):903-909.
Grubb et al., "Chemically modified beta-glucuronidase crosses blood-brain barrier and clears neuronal storage in murine mucopolysaccharidosis VII," *Proc. Natl. Acad. Sci. USA*, 2008, 105(7):2616-2621.
Grubb et al., "New Strategies for Enzyme Replacement Therapy for Lysosomal Storage Diseases," *Rejuvenation Research*, 2010, 13(2-3):229-236.
Jones et al., "Oropharyngeal dysphagia in infants and children with infantile Pompe disease," *Dysphagia*, 2010, 25:277-283.
Kishnani et al., "Chinese hamster ovary cell-derived recombinant human acid alpha-glucosidase in infantile-onset Pompe disease," *J. Pediatr.*, 2006,149:89-97.

(Continued)

*Primary Examiner* — Wu-Cheng Winston Shen
*Assistant Examiner* — Yih-Horng Shiao
(74) *Attorney, Agent, or Firm* — Womble Carlyle Sandridge & Rice, LLP

(57) ABSTRACT

Methods of treating a lysosomal storage disorder and methods of increasing cellular uptake of a lysosomal enzyme using β2 agonists or therapeutic agents that increase expression of receptors for a lysosomal enzyme.

17 Claims, 21 Drawing Sheets

(56) References Cited

OTHER PUBLICATIONS

Kishnani et al., "Recombinant human acid {alpha}-glucosidase: Major clinical benefits in infantile-onset Pompe disease,"*Neurology*, 2007, 68:99-109.

Kishnani et al., "Cross-reactive immunologic material status affects treatment outcomes in Pompe disease infants," *Mol. Genet. Metab.*, 2010, 99:26-33.

Kobayashi et al., "Prognostic factors for the late onset Pompe disease with enzyme replacement therapy: from our experience of 4 cases including an autopsy case," *Mol. Genet. Metab.*, 2010, 100(1):14-19.

Koeberl et al., "Enhanced efficacy of enzyme replacement therapy in Pompe disease through mannose-6-phosphate receptor expression in skeletal muscle," *Mol. Genet. Metab.*, 2011, 103:107-112.

Koeberl et al., "β2 agonists enhance the efficacy of simultaneous enzyme replacement therapy in murine Pompe disease," *Mol. Genet. Metab.*, 2012, 105(2): 221-227 [E-pub Nov. 11, 2011].

Lynch et al., "Role of beta-adrenoceptor signaling in skeletal muscle: implications for muscle wasting and disease," *Physiol. Rev.*, 2008, 88(2):729-767.

Maclennan et al., "Effects of clenbuterol and propranolol on muscle mass. Evidence that clenbuterol stimulates muscle beta-adrenoceptors to induce hypertrophy," *Biochem. J.*, 1989, 264(2):573-579.

Matsumoto et al.,"The expressions of insulin-like growth factors, their receptors, and binding proteins are related to the mechanism regulating masseter muscle mass in the rat," *Arch. Oral. Biol.*, 2006, 51(7):603-611.

McCarty et al., "Mannitol-facilitated CNS entry of rAAV2 vector significantly delayed the neurological disease progression in MPS IIIB mice," *Gene Ther.*, 2009, 16(11):1340-1352.

McVie-Wylie et al., "Biochemical and pharmacological characterization of different recombinant acid alpha-glucosidase preparations evaluated for the treatment of Pompe disease," *Mol. Genet. Metab.*, 2008, 94: 448-455.

Morissette et al., "Myostatin inhibits IGF-I-induced myotube hypertrophy through Akt," *Am. J. Physiol. Cell. Physiol.*, 2009, 297(5):C1124-1132.

Mounier et al., "Molecular impact of clenbuterol and isometric strength training on rat EDL muscles," *Pflugers. Arch.*, 2007, 453(4):497-507.

Nicolino et al., "Clinical outcomes after long-term treatment with alglucosidase alfa in infants and children with advanced Pompe disease," *Genet. Med.*, 2009,11(3):210-219.

Oya et al., "Adult form of acid maltase deficiency presenting with pattern of muscle weakness resembling facioscapulohumeral dystrophy," *Rinsho Shinkeigaku*, 2001, 41(7):390-396 (abstract only).

Plant et al., "Therapeutic clenbuterol treatment does not alter Ca2+ sensitivity of permeabilized fast muscle fibres from exercise trained or untrained horses," *J. Muscle Res. Cell Motil.*, 2003, 24(7):471-476.

Polito et al., "IDS crossing of the blood-brain barrier corrects CNS defects in MPSII mice," *Am. J. Hum. Genet.*, 2009, 85(2):296-301.

Ponce et al., "Murine acid alpha-glucosidase: cell-specific mRNA differential expression during development and maturation," *Am. J. Pathol.*, 1999, 154(4):1089-1096.

Raben et al., "Conditional tissue-specific expression of acid alpha-glucosidase (GAA) gene in the GAA knockout mice: implications for therapy," *Human Mol. Genet.*, 2001, 10(19):2039-2047.

Raben et al., "Glycogen stored in skeletal but not in cardiac muscle in acid alpha-glucosidase mutant (Pompe) mice is highly resistant to transgene-encoded human enzyme," *Mol Ther.*, 2002, 6(5):601-608.

Raben et al.,"Induction of tolerance to a recombinant human enzyme, acid alpha-glucosidase, in enzyme deficient knockout mice," *Transgenic Res.*, 2003, 12(2):171-178.

Raben et al., "Enzyme replacement therapy in the mouse model of Pompe disease," *Mol. Genet. Metab.*, 2003, 80(1-2):159-169.

Raben et al., "Replacing acid alpha-glucosidase in Pompe disease: Recombinant and transgenic enzymes are equipotent, but neither completely clears glycogen from type II muscle fibers," *Mol. Ther.*, 2005, 11(1):48-56.

Ryall et al., "Beta 2-agonist administration reverses muscle wasting and improves muscle function in aged rats," *J. Physiol.*, 2004, 555:175-888.

Ryall et al., "Systemic administration of beta2-adrenoceptor agonists, formoterol and salmeterol, elicit skeletal muscle hypertrophy in rats at micromolar doses," *Br. J. Pharmacol.*, 2006, 147:587-595.

Ryall et al., "The potential and the pitfalls of beta-adrenoceptor agonists for the management of skeletal muscle wasting," *Pharmacol. Ther.*, 2008, 120(3):219-232.

Sandri, "Signaling in muscle atrophy and hypertrophy," *Physiology*, 2008, 23:160-170.

Shi et al., "Extracellular signal-regulated kinase pathway is differentially involved in beta-agonist-induced hypertrophy in slow and fast muscles," *Am. J. Physiol. Cell Physiol.*, 2007, 292(5):C1681-C1689.

Strothotte et al., "Enzyme replacement therapy with alglucosidase alfa in 44 patients with late-onset glycogen storage disease type 2: 12-month results of an observational clinical trial," *J. Neurol.*, 2010, 257(1):91-97.

Sun et al., "Efficacy of an adeno-associated virus 8-pseudotyped vector in glycogen storage disease type II," *Mol. Ther.*, 2005, 11(1):57-65.

Sun et al., "Correction of glycogen storage disease type II by an adeno-associated virus vector containing a muscle-specific promoter," *Mol. Ther.*, 2005,11(6):889-898.

Sun et al., "Antibody formation and mannose-6-phosphate receptor expression impact the efficacy of muscle-specific transgene expression in murine Pompe disease," *J. Gene Med.*, 2010, 12(11):881-91.

Thurberg et al.,"Characterization of pre- and post-treatment pathology after enzyme replacement therapy for Pompe disease," *Lab Invest.*, 2006, 86(12):1208-1220.

Van Hove et al., "High-level production of recombinant human lysosomal acid alpha-glucosidase in Chinese hamster ovary cells which targets to heart muscle and corrects glycogen accumulation in fibroblasts from patients with Pompe disease." *Proc. Natl. Acad. Sci. USA*, 1996, 93(1):65-70.

Wraith et al., "Mucopolysaccharidosis type II (Hunter syndrome): a clinical review and recommendations for treatment in the era of enzyme replacement therapy," *Eur J Pediatr*, 2008, 167(3):267-277.

Wylie et al., "Tissue-specific inactivation of murine M6P/IGF2R." *Am. J. Pathol.*, 2003, 162(1):321-328.

Yanovitch et al., "Clinical and histologic ocular findings in pompe disease."*J. Pediatr. Ophthalmol. Strabismus*, 2010, 47(1):34-40.

Zhu et al., "Carbohydrate-remodelled acid alpha-glucosidase with higher affinity for the cation-independent mannose 6-phosphate receptor demonstrates improved delivery to muscles of Pompe mice," *Biochem J.*, 2005, 389: 619-628.

Zhu et al., "Glycoengineered acid alpha-glucosidase with improved efficacy at correcting the metabolic aberrations and motor function deficits in a mouse model of Pompe disease." *Mol. Ther.*, 2009,17(6):954-963.

* cited by examiner

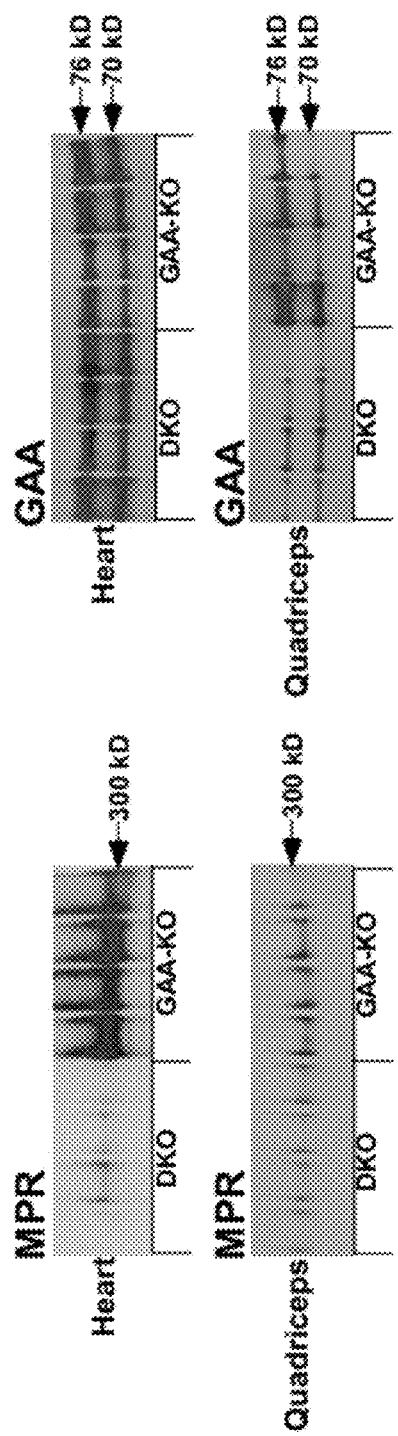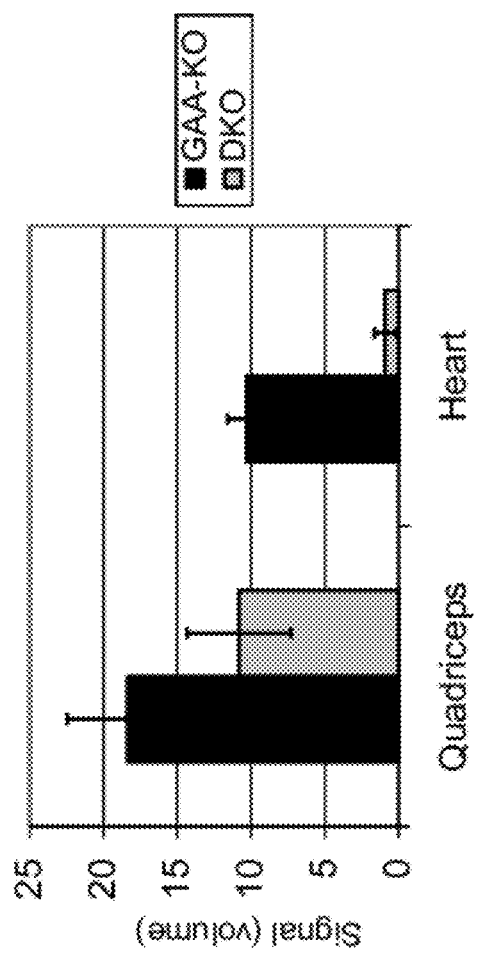
FIG 2A
FIG 2B

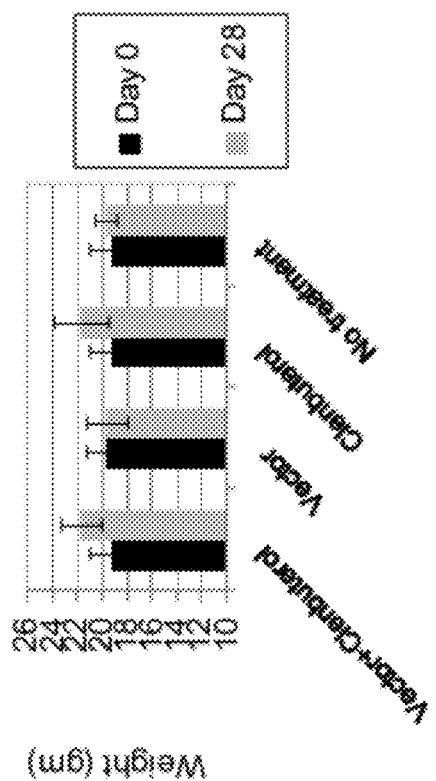
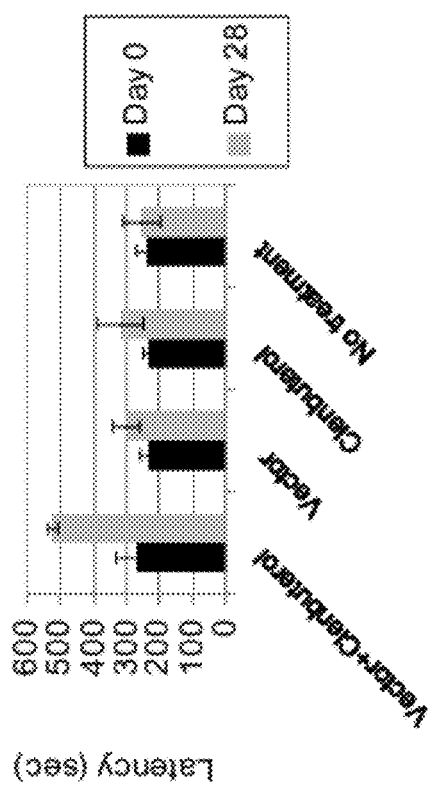
FIG 4B
FIG 4A

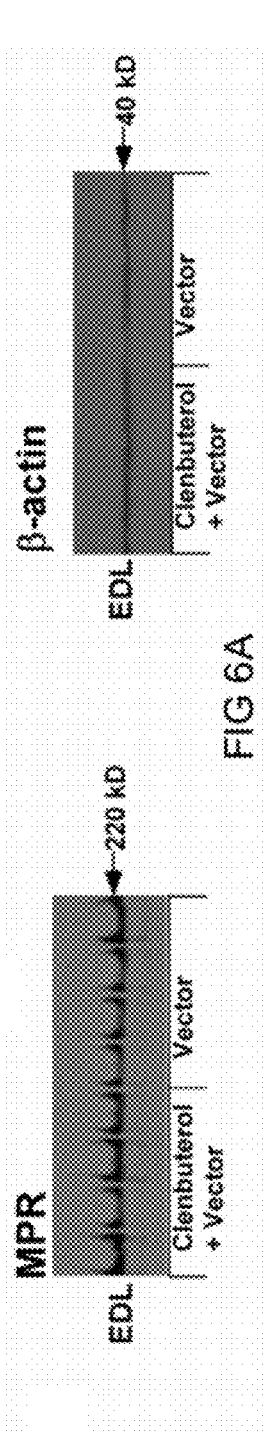
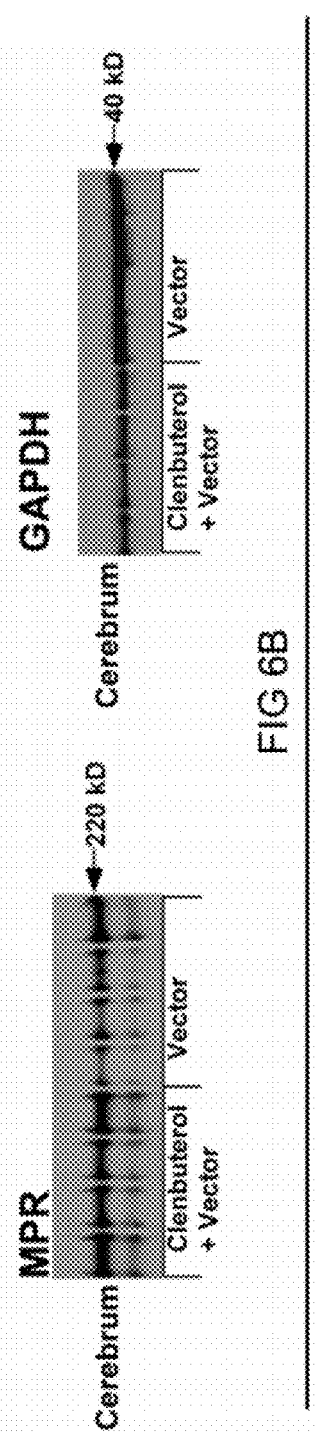
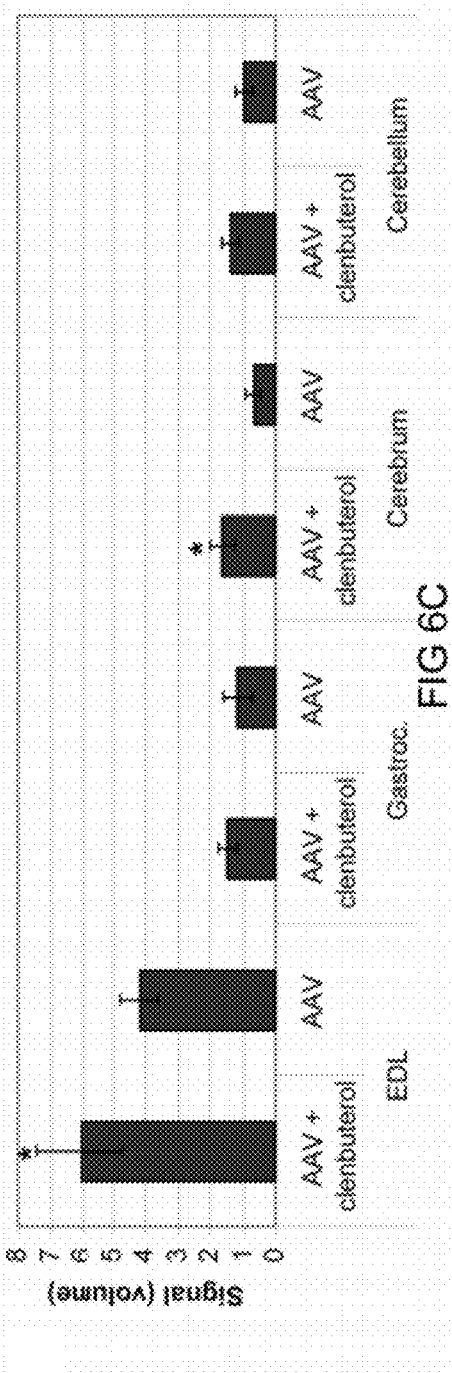
FIG 6A
FIG 6B
FIG 6C

METHODS OF LYSOSOMAL STORAGE DISEASE THERAPY

RELATED APPLICATIONS

Priority is claimed to U.S. Provisional Application No. 61/420,828, filed 8 Dec. 2010, and to U.S. Provisional Application No. 61/389,494, filed 4 Oct. 2010, each of which is incorporated herein in its entirety.

FEDERAL FUNDING

This disclosure was produced in part using funds from the Federal Government under NIH grant no. R01 HL081122-03 entitled "Gene Delivery to Striated Muscle by Systematic AAV Vectors." Accordingly, the Federal government has certain rights in this disclosure.

FIELD OF THE INVENTION

The present disclosure generally relates to treatment of lysosomal storage diseases. More particularly, it relates to methods of enhancing expression of receptors for lysosomal enzymes to thereby treat lysosomal storage diseases.

BACKGROUND

The lysosomal storage disorders (LSDs) are characterized by deficiencies in lysosomal enzymes resulting from mutations in genes that encode the enzyme proteins and related cofactors. Lysosomal enzymes degrade most biomolecules, the products of which are then recycled in a process that is essential for cell health and growth. LSDs result in accumulation of undegraded products in lysosomes and concomitant cell enlargement, dysfunction, and death. The clinical manifestations of LSDs include neuronal lipidosis, leukodystrophy, mucopolysaccharidosis, and storage histiocytosis.

Pompe disease (Glycogen storage disease type II; acid maltase deficiency; MIM 232300) is a myopathy, similar to limb-girdle muscular dystrophy in its late-onset form, which results from acid α-glucosidase (GAA) deficiency in striated and smooth muscle. Enzyme replacement therapy (ERT) with recombinant human GAA (rhGAA) has been effective in a subset of patients with Pompe disease. Infantile-onset Pompe disease affects the heart and skeletal muscle primarily, and causes death early in childhood from cardiorespiratory failure related to an underlying hypertrophic cardiomyopathy, if initiation of ERT is delayed or the patient fails to respond sustainably due to high, sustained anti-GAA antibodies. See Hirschhorn & Reuser, "Glycogen Storage Disease Type II: Acid Alpha-Glucosidase (acid maltase) Deficiency," in Scriver et al. (Eds.), *The Metabolic & Molecular Bases of Inherited Diseases*, 2001, New York: McGraw-Hill, pp. 3389-3420; Kishnani et al., *J. Pediatr.*, 2006, 149:89-97; Kishnani et al., *Mol. Genet. Metab.*, 2010, 99:26-33.

GAA normally functions as an acid hydrolase that metabolizes lysosomal glycogen, and GAA deficiency causes lysosomal glycogen accumulation in virtually all tissues (Ponce et al., *Am. J. Pathol.*, 1999, 154:1089-1096). The availability of ERT with rhGAA has prolonged survival and ameliorated the cardiomyopathy of infantile Pompe disease (Kishnani et al., *Neurology*, 2007, 68:99-109). In late-onset Pompe disease ERT has largely resulted in stabilization of the disease process from a pulmonary and motor perspective (Case et al., *Mol. Genet. Metab.*, 2008, 95:233-235). Documented limitations of ERT in Pompe disease include the requirement for frequent intravenous infusions of high levels of GAA to achieve efficacy, degree of pre-ERT muscle damage, and the possibility of humoral immunity (Kishnani et al., *Mol. Genet. Metab.*, 2010, 99:26-33; Amalfitano et al., *Genet. Med.*, 2001, 3:132-138). The rhGAA doses are markedly higher than doses required for ERT in other lysosomal storage disorders, reflecting the high threshold for correction of GAA deficiency in the skeletal muscle of Pompe disease patients (Desnick, *J. Inherit. Metab. Dis.*, 2004, 27:385-410).

Even in CRIM-positive infants with Pompe disease, a lack of complete efficacy from ERT has been observed. Children with Pompe disease have residual motor developmental delays and respiratory insufficiency (Nicolino et al., *Genet. Med.*, 2009, 11:210-219). Hypernasal speech and swallowing difficulties indicated residual oromotor abnormalities despite long-term ERT in infantile-onset Pompe disease (Jones et al., *Dysphagia*, 2010, 25:277-283). Many young children with Pompe disease require temporary or long-term assisted ventilation (Nicolino et al., *Genet. Med.*, 2009, 11:210-219). Strabismus and ptosis have been observed frequently among children with Pompe disease, while receiving ERT (Yanovitch et al., *J. Pediatr. Ophthalmol. Strabismus*, 2010, 47:34-40). Each of these abnormalities demonstrates a lack of complete efficacy from ERT. Patients with late-onset Pompe disease have severe pulmonary insufficiency may progress to respiratory failure while receiving ERT (Kobayashi et al., *Mol. Genet. Metab.*, 2010, 100:14-19). Many individuals with late-onset Pompe disease have residual gait abnormalities despite adherence to ERT, indicating a relative lack of response of leg muscles (Strothotte et al., *J. Neurol.*, 2010, 257:91-97).

Accordingly, there exists a continuing need for new therapies for lysosomal storage diseases, such as Pompe disease. The present invention provides therapeutic strategies premised upon increased expression of cell surface receptors that bind to lysosomal enzymes. This approach may be effective as a stand alone therapy or for enhancement of other therapies, such as ERT.

SUMMARY OF THE INVENTION

The present invention provides methods of treating a patient having a lysosomal storage disease characterized by reduced or deficient activity of a lysosomal enzyme comprising increasing expression of receptors for the lysosomal enzyme in the patient. Also provided are methods of treating a patient having a lysosomal storage disease characterized by reduced or deficient activity of a lysosomal enzyme comprising (a) identifying a patient that has received or will receive enzyme replacement therapy; and (b) increasing expression of receptors for the lysosomal enzyme in the patient.

In other aspects of the invention are provided methods of treating a patient having a lysosomal storage disease characterized by reduced or deficient activity of a lysosomal enzyme comprising administering a β2 agonist to the patient. Also provided are methods of treating a patient having a lysosomal storage disease characterized by reduced or deficient activity of a lysosomal enzyme comprising (a) identifying a patient that has received or will receive enzyme replacement therapy; and (b) administering a β2 agonist to the patient.

In other aspects of the invention are provided methods of increasing cellular uptake of a lysosomal enzyme in a patient by increasing expression of receptors for the lysosomal enzyme in the patient or by administering a β2 agonist to the patient.

In any of the disclosed methods, the patient can be a human patient.

In any of the disclosed methods, the lysosomal storage disease to be treated can be Pompe disease, adult-onset glycogen storage disease II (GSD II), Gaucher disease, Fabry disease, mucopolysaccharidosis type I, mucopolysaccharidosis type II, or Niemann-Pick disease. Optionally, the lysosomal storage disease to be treated is characterized by reduced or deficient activity of the lysosomal enzyme in the brain of the patient.

In particular aspects of the disclosed methods, the lysosomal enzyme that is deficient in a patient to be treated is acid α-glucosidase.

In other particular aspects of the invention, the disclosed treatment methods are performed by increasing expression of receptors for a lysosomal enzyme in the patient, wherein the receptors are Cation Independent Mannose-6-Phosphare Receptors (CI-MPR).

In any of the disclosed methods, expression of receptors for a lysosomal enzyme can be increased by administering a β2 agonist (e.g., clenbuterol, formoterol, salmeterol, albuterol, and combinations thereof), growth hormone (e.g., human growth hormone), autocrine glycoprotein (e.g., Follistatin), or combination thereof, to the patient. These agents may be administered to the patient in any suitable manner, including orally, intranasally, intravenously, intramuscularly, or transdermally.

In performing the disclosed methods, levels of receptors for the lysosomal enzyme are increased in the patient. Where the lysosomal storage disorder is characterized by brain involvement, levels of the lysosomal receptor are increased in brain.

In some aspects of the invention, increasing expression of receptors for a lysosomal enzyme is used in combination with enzyme replacement therapy, for example, administration and expression of a vector encoding the lysosomal enzyme in the patient. Useful vectors include viral vectors, such as an adeno-associated virus (AAV) vector. The patient can receive enzyme replacement therapy prior to, concurrently with, or subsequent to, increasing expression of receptors for the lysosomal enzyme in the patient. In such combination therapies, the efficacy of the enzyme replacement therapy is enhanced, including efficacy of the enzyme replacement in brain. For example, the activity of the lysosomal enzyme in the patient is increased to a level greater than that observed in a patient receiving enzyme replacement therapy alone or in a patient prior to increasing expression of receptors for the lysosomal enzyme. Where increasing expression of receptors for the lysosomal enzyme is performed by administering a β2 agonist, the activity of the lysosomal enzyme in the patient is increased to a level greater than that observed in a patient receiving enzyme replacement therapy alone or receiving the β2 agonist alone.

In a particular aspect of the invention is provided a method of treating a patient having a lysosomal storage disease characterized by reduced or deficient activity of acid α-glucosidase, for example, Pompe disease or adult-onset glycogen storage disease II (GSD II), by administering a β2 agonist to the patient. In a related aspect of the invention is provided a method of treating a patient having Pompe disease characterized by reduced or deficient activity of acid α-glucosidase by (a) identifying a patient that has received or will receive acid α-glucosidase replacement therapy; and (b) administering a β2 agonist to the patient. Representative β2 agonists include clenbuteral and albuterol. In accordance with the disclosed methods, levels of Cation Independent Mannose-6-Phosphare Receptors (CI-MPR) are increased in the patient, activity of acid α-glucosidase is increased in the patient, and/or levels of glycogen are decreased in the patient.

BRIEF DESCRIPTION OF THE DRAWINGS

FIG. 1A shows GAA enzyme levels and FIG. 1B shows glycogen content evaluated in the target tissues. Mean+/−standard deviation are shown.

FIG. 2A-2B depicts the western blot analysis of CI-MPR (MPR) expression and GAA content of heart and skeletal muscle. FIG. 2A shows Western blot detection of CI-MPR and human GAA in the tissues of DKO and GAA-KO mice, with molecular weights indicated. Each lane represents an individual mouse. FIG. 2B shows signal for CI-MPR as quantified by densitometry of Western blots. CI-MPR expression was significantly reduced in the heart and quadriceps of DKO mice, in comparison with GAA-KO mice. Mean+/−standard deviation are shown.

FIG. 3A shows GAA enzyme levels and FIG. 3B shows glycogen content evaluated in the target tissues. Mean+/−standard deviation are shown. Statistically significant differences indicated (*=$p<0.05$; **=$p<0.01$).

FIG. 4A-4B depicts enhanced Rotarod performance and weight gain following liver-targeted gene therapy plus clenbuterol treatment. The GAA-KO mice (5 per group) were injected with AAV-LSPhGAA ($2 \times 10^{10}$ vector particles/mouse). Vector treated mice were treated with clenbuterol or untreated. Non-vector treated GAA-KO mice were treated with clenbuterol or untreated to serve as controls. Mice were euthanized for tissue analysis 4 weeks after vector injection. FIG. 4A shows Rotarod latency performance and FIG. 4B shows weight at the indicated time points. Mean+/−standard deviation are shown. Statistically significant differences indicated (*=$p<0.05$; **=$p<0.01$).

FIG. 5A shows GAA enzyme levels and FIG. 5B shows glycogen content evaluated in the target tissues. Statistically significant differences indicated (*=$p<0.05$; **=$p<0.01$).

FIG. 6A-6C shows Western blot analysis of CI-MPR expression of skeletal muscle and brain. Western blot detection of CI-MPR and control proteins, β-actin or glyceraldehydes-3-phosphate dehydrogenase (GAPDH) in the tissues of GAA-KO mice is shown, with molecular weights indicated. Each lane represents an individual mouse. Equivalent quantities of tissue homogenate were loaded for each mouse. FIG. 6A shows EDL. FIG. 6B shows cerebrum. FIG. 6C shows the signal for CI-MPR as quantified by densitometry of Western blots. Mean+/−standard deviation are shown. Statistically significant differences indicated (*=p<0.05; **=p<0.01).

FIG. 7A shows Rotarod latency performance and FIG. 7B shows weight at indicated time points. Mean+/−standard deviation are shown. Statistically significant differences indicated (*=p<0.05; **=p<0.01).

FIG. 8A shows GAA activity of liver and spleen. FIG. 8B shows GAA enzyme levels in the skeletal muscles. FIG. 8C shows glycogen content was evaluated in the skeletal muscles. Mean+/−standard deviation are shown. Statistically significant differences indicated (*=p<0.05; **=p<0.01).

FIG. 10A shows Rotarod latency at the indicated times. FIG. 10B shows wire hang latency. FIG. 10C shows weight of gastrocnemius. Mean+/−standard deviation are shown. P values indicate statistically significant differences (lines).

FIG. 11A shows GAA enzyme levels and FIG. 11B glycogen content evaluated in skeletal muscle, including the quadriceps, gastrocnemius (Gastroc.), tibialis anterior (Tib. Ant.), EDL, and soleus. Statistically significant alterations associated with clenbuterol treatment indicated (*=p<0.05; **=p<0.001).

FIG. 12A shows GAA enzyme levels and FIG. 12B glycogen content. Statistically significant alterations associated with clenbuterol treatment indicated (*=p<0.05; **=p<0.001).

DETAILED DESCRIPTION OF THE INVENTION

Figure 1A:
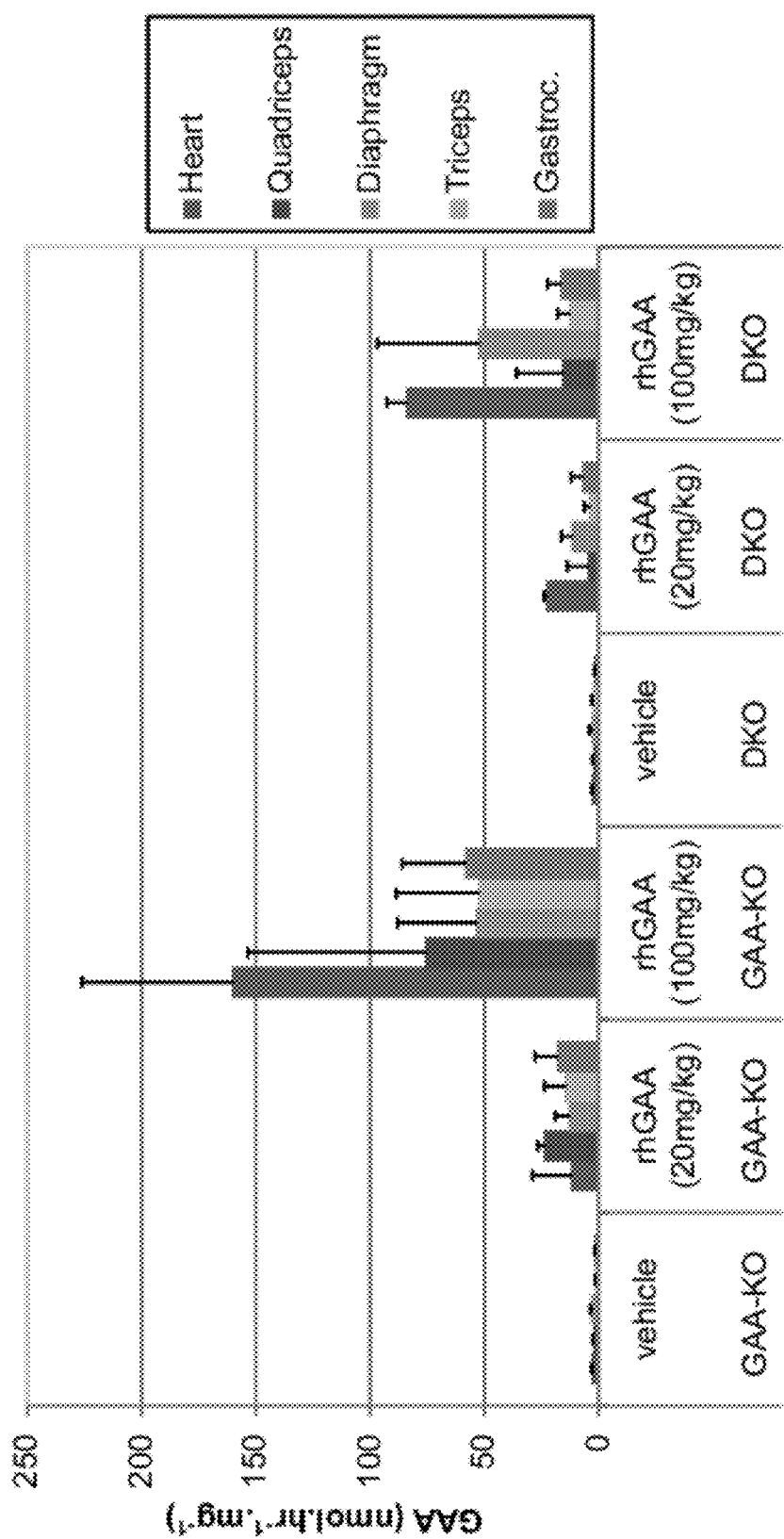
FIG. 1A-1B depicts the impaired rhGAA uptake and impaired glycogen clearance in CI-MPR-KO/GAA-KO (double (D) KO) mice. The homozygous DKO mice (n=4) and GAA-KO (Pompe disease) mice (n=4) were administered four weekly doses of 20 mg/kg and 100 mg/kg body weight of rhGAA and sacrificed three days after the last injection.

The present disclosure encompasses methods of treating lysosomal storage diseases by up-regulating lysosomal enzyme receptors to thereby increase uptake of beneficial enzymes into target cells.

Lysosomal storage diseases include any disorder characterized by reduced or absent lysosomal enzyme activity. Representative lysosomal storage diseases include Pompe disease, including adult-onset/late-onset glycogen storage disease II, Gaucher disease, Fabry disease, Schindler disease, Niemann-Pick disease (including Type A, Type B, and Type C), Morquio disease (including Type A and Type B), Batten disease, Maroteaux-Lamy disease, metachromatic leukodystrophy disease, Hunter Syndrome, and Hurler Syndrome (including Hurler-Scheie Syndrome). Additional representative lysosomal storage diseases that may be treated using the disclosed methods include Activator Deficiency/GM2 Gangliosidosis, Alpha-mannosidosis, Aspartylglucosaminuria, Cholesteryl ester storage disease, Chronic Hexosaminidase A Deficiency, Cystinosis, Danon disease, Farber disease, Fabry disease, Fucosidosis, Galactosialidosis (including Type I, Type II, and Type III), GM1 gangliosidosis, I-Cell disease/Mucolipidosis II, Infantile Free Sialic Acid Storage Disease/ISSD, Juvenile Hexosaminidase A Deficiency, Krabbe disease, Lysosomal acid lipase deficiency, Mucopolysaccharidoses disorders, Pseudo-Hurler polydystrophy/Mucolipidosis IIIA, Scheie Syndrome, Sanfilippo syndrome (including Type A, Type B, Type C, and Type D), MPS VII Sly Syndrome, mucopolysaccharidosis type I, mucopolysaccharidosis type II, Mucolipidosis I/Sialidosis, Mucolipidosis IIIC, Mucolipidosis type IV, Multiple sulfatase deficiency, Neuronal Ceroid Lipofuscinoses, CLN6 disease, Finnish Variant Late Infantile CLN5, Jansky-Bielschowsky disease/Late infantile CLN2/TPP1 Disease, Kufs/Adult-onset NCL/CLN4 disease, Northern Epilepsy/variant late infantile CLN8, Santavuori-Haltia/Infantile CLN1/PPT disease, Beta-mannosidosis, Pycnodysostosis, Sandhoff disease/Adult Onset/GM2 Gangliosidosis, Sandhoff disease/GM2 gangliosidosis, Salla disease/Sialic Acid Storage Disease, Tay-Sachs/GM2 gangliosidosis, and Wolman disease. Patients having a lysosomal disease may show partial or incomplete enzyme activity. The methods disclosed herein are also useful for treatment of lysosomal storage disorders that feature severe brain involvement.

As used herein, the terms "treat" and "treatment" refer to the alleviation, e.g., amelioration of one or more symptoms or effects associated with the disease, prevention, inhibition or delay of the onset of one or more symptoms or effects of the disease, lessening of the severity or frequency of one or more symptoms or effects of the disease, and/or increasing or trending toward desired outcomes as described herein.

Desired outcomes of the treatments disclosed herein vary according to the lysosomal storage disease and are readily determinable to those skilled in the art. Generally, desired outcomes include measurable indices such as increased lysosomal enzyme uptake and/or activity, decreased enzyme metabolite accumulation, increased expression and/or cell surface density of lysosomal enzyme receptors (e.g., mannose receptors (MR), asialoglycoprotein receptors (ASGPR) and CI-MPR), and improved motor functions.

As one example, desired outcomes for the treatment of Pompe disease include improved delivery of rhGAA or GAA to cardiac, skeletal muscle, and brain cells, increased GAA activity in muscle and brain tissues, and decreased glycogen accumulation in these same tissues. Additional desired outcomes for Pompe disease include improvement of cardiac status or of pulmonary function; improvement in neurodevelopment and/or motor skills; or a prevention, delay, lessening or reversal of other manifestations of the disorder. For example, in infants (in which typically less than 1% of normal acid alpha-glucosidase activity is present), Pompe disease patients are affected by a hypertrophic cardiomyopathy, generalized muscle weakness and hypotonia secondary to massive glycogen accumulation in cardiac and skeletal muscles. The disease progresses rapidly, with death from cardiac failure usually occurring by one year of age. Juveniles (1-10% of normal acid alpha-glucosidase activity) and adults (10-40% of normal acid alpha-glucosidase activity) with Pompe disease are characterized by lack of severe cardiac involvement, later age of onset, and slower progression. Their eventual respiratory or limb muscle failures results in significant morbidity and mortality. Desired outcomes of methods for treating Pompe disease include a decrease in the incidence or severity of the above-noted effects.

Desired outcomes of the disclosed therapies are generally quantifiable measures as compared to a control or baseline measurement. As used herein, relative terms such as "improve," "increase," or "reduce" indicate values relative to a control, such as a measurement in the same individual prior to initiation of treatment described herein, or a measurement in a control individual (or multiple control individuals) in the absence of the treatment described herein. A control individual is an individual afflicted with the same form of lysosomal storage disease as the individual being treated, who is about the same age as the individual being treated (to ensure that the stages of the disease in the treated individual and the control individual are comparable).

Changes or improvements in response to therapy are generally statistically significant. As used herein, the term "significance" or "significant" relates to a statistical analysis of the probability that there is a non-random association between two or more entities. To determine whether or not a relationship is "significant" or has "significance," statistical manipulations of the data can be "p-value." Those p-values that fall below a user-defined cut-off point are regarded as significant. A p-value less than or equal to 0.1, less than 0.05, less than 0.01, less than 0.005, or less than 0.001 may be regarded as significant.

Patients or subjects amenable to the therapies disclosed herein include both human and non-human animals having a lysosomal storage disease, including disorders characterized by a partial enzyme deficiency, or at risk of a lysosomal storage disease. At-risk patients may be identified by analysis of relevant genetic mutations associated with lysosomal storage disease and/or by biochemical profiling, for example, to detect reduced levels of lysosomal enzyme activity. Representative patients include humans, nonhuman primates, sheep, dog, cat, horse, cow, chickens, amphibians, reptiles, and the like.

According to the disclosed methods, a patient having a lysosomal storage disease is treated by increasing expression of receptors for the lysosomal enzyme, or otherwise increasing cell surface density of such receptors, in the patient. Representative therapeutic agents capable of inducing such increased expression include growth hormone (e.g., human growth hormone), autocrine glycoproteins (e.g., Follistatin), and β2 agonists. Such therapeutic agents may selectively modulate expression of receptors for particular lysosomal enzymes. Expression of receptors for a lysosomal enzyme may also be increased by behaviors, such as exercise. In one aspect of the invention, a β2 agonist is administered to a patient suffering from adult-onset or late-onset glycogen storage disease II, or a patient who presents with only partial enzyme deficiency, wherein administering the β2 agonist results in biochemical correction of the enzyme deficiency in target tissues (including muscle and brain) and improved motor function.

β2 agonists are molecules that stimulate the β2-adrenergic receptor. Numerous β2 agonists are known in the art and may be used in the therapeutic methods of the invention. Representative β2 agonists include albuterol, arbutamine, bambuterol, befunolol, bitolterol, bromoacetylalprenololmenthane, broxaterol, carbuterol, cimaterol, cirazoline, clenbuterol, clorprenaline, denopamine, dioxethedrine, dopexamine, ephedrine, epinephrine, etafedrine, ethylnorepinephrine, etilefrine, fenoterol, formoterol, hexoprenaline, higenamine, ibopamine, isoetharine, isoproterenol, isoxsuprine, mabuterol, metaproterenol, methoxyphenamine, norepinephrine, nylidrin, oxyfedrine, pirbuterol, prenalterol, procaterol, propranolol, protokylol, quinterenol, ractopamine, reproterol, rimiterol, ritodrine, salmefamol, soterenol, salmeterol, terbutaline, tretoquinol, tulobuterol, xamoterol, zilpaterol, zinterol. Optionally, β2 agonists used in the disclosed methods do not interact, or show substantially reduced interaction, with β1-adrenergic receptors.

According to the invention, a patient having a lysosomal storage disease is administered an effective amount of a therapeutic agent, i.e., an amount sufficient for treatment or to achieve a desired outcome. For example, about 0.1-50 mg/kg of a therapeutic agent/body weight of the patient can be administered, such as about 1-10 mg/kg, or about 0.1-5 mg/kg, or at least about 10 mg/kg. The effective amount for a particular individual can be varied (e.g., increased or decreased) over time, depending on the needs of the individual.

Administering of a therapeutic agent useful in the disclosed methods may be performed by any suitable route, including administration by inhalation or insufflation (either through the mouth or the nose) or oral, sublingual, buccal, parenteral, topical, subcutaneous, intraperitoneal, intravenous, intrapleural, intraoccular, intraarterial, rectal administration, or within/on implants, e.g., matrices such as collagen fibers or protein polymers, via cell bombardment, in osmotic pumps, grafts comprising appropriately transformed cells, etc. In particular, the disclosed therapeutic methods and agents are useful for treating lysosomal storage diseases characterized by severe brain involvement without the need for invasive administration techniques directly to brain (e.g., intrathecal administration).

A therapeutic agent capable of enhancing expression of receptors for a lysosomal enzyme can be administered to the patient as a pharmaceutical composition comprising the therapeutic agent and a pharmaceutically acceptable carrier or excipient. The preparation of a pharmacological composition that contains active ingredients dissolved or dispersed therein is well understood in the art. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent. Among the acceptable vehicles and solvents that may be employed are water, Ringer's solution and isotonic sodium chloride solution. In addition, solid forms suitable for solution, or suspensions, in liquid prior to use can also be prepared. Formulation also varies according to the route of administration selected (e.g., solution, emulsion, capsule).

Pharmaceutically acceptable carriers can include inert ingredients which do not interact with the β2 agonist, lysosomal enzyme and/or other additional therapeutic agents. These carriers include sterile water, salt solutions (e.g., NaCl), physiological saline, bacteriostatic saline (saline containing about 0.9% benzyl alcohol), phosphate-buffered saline, Hank's solution, Ringer's-lactate saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, dextrose, lactose, trehalose, maltose or galactose, magnesium stearate, talc, silicic acid, viscous paraffin, perfume oil, fatty acid esters, hydroxymethylcellulose and polyvinyl pyrolidone, as well as combinations thereof. The compositions may be mixed with auxiliary agents, e.g., lubricants, preservatives, stabilizers, wetting agents, emulsifiers, salts for influencing osmotic pressure, pH buffers, coloring, flavoring and/or aromatic substances and the like which do not deleteriously react with the active compounds. In addition, the compositions of the invention may be lyophilized (and then rehydrated) in the presence of such excipients prior to use.

Standard pharmaceutical formulation techniques as known in the art can be employed, such as those described in Remington's Pharmaceutical Sciences, Mack Publishing Company, Easton, Pa. Methods for encapsulating compositions. The composition can be a liquid solution, suspension, emulsion, tablet, pill, capsule, sustained release formulation, or powder. The composition can also be formulated as a suppository, with traditional binders and carriers such as triglycerides. Oral formulation can include standard carriers such as pharmaceutical grades of mannitol, lactose, starch, magnesium stearate, polyvinyl pyrollidone, sodium saccharine, cellulose or magnesium carbonate. For example, a composition for intravenous administration typically is a solution in a water-soluble carrier, e.g., sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is administered by injection, an ampule of sterile water for injection or saline can be provided so that the ingredients may be mixed prior to administration.

A therapeutic agent capable of enhancing expression of receptors for a lysosomal enzyme can be administered as a neutral compound or as a salt or ester. Pharmaceutically acceptable salts include those formed with free amino groups such as those derived from hydrochloric, phosphoric, acetic, oxalic or tartaric acids, and those formed with free carboxyl groups such as those derived from sodium, potassium, ammonium, calcium, ferric hydroxides, isopropylamine, triethylamine, 2-ethylamino ethanol, histidine, and procaine. For instance, salts of compounds containing an amine or other basic group can be obtained by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base such as a hydroxide base. Salts of acidic functional groups contain a countercation such as sodium or potassium.

Also encompassed by the instant disclosure are methods of increasing efficacy of a lysosomal storage disease therapy, e.g., substrate deprivations and small molecule therapies, lysosomal enzyme replacement therapy, including gene therapy (e.g., transfection of cells in a patient with a vector encoding a deficient lysosomal enzyme), or any other form of therapy where the levels of the deficient lysosomal enzyme in a patient are supplemented. For example, these therapies may comprise (a) identifying a patient that has received or will receive enzyme replacement therapy; and (b) increasing expression of receptors for a lysosomal enzyme, for example, by administering an effective amount of β2 agonist.

Thus, in some aspects of the invention, a therapeutic agent capable of increasing expression of receptors for a lysosomal enzyme is administered in combination with a second therapeutic agent or treatment, and in such cases, the therapeutic agents or treatments may be administered concurrently or consecutively in either order. For concurrent administration, the therapeutic agents may be formulated as a single composition or as separate compositions. The optimal method and order of administration of the therapeutic agents capable of increasing expression of a receptor for a lysosomal enzyme and a second therapeutic agent or treatment can be ascertained by those skilled in the art using conventional techniques and in view of the information set out herein.

The disclosed combination therapies may elicit a synergistic therapeutic effect, i.e., an effect greater than the sum of their individual effects or therapeutic outcomes. Measurable therapeutic outcomes are described herein. For example, a synergistic therapeutic effect may be an effect of at least about two-fold greater than the therapeutic effect elicited by a single agent, or the sum of the therapeutic effects elicited by the single agents of a given combination, or at least about five-fold greater, or at least about ten-fold greater, or at least about twenty-fold greater, or at least about fifty-fold greater, or at least about one hundred-fold greater. A synergistic therapeutic effect may also be observed as an increase in therapeutic effect of at least 10% compared to the therapeutic effect elicited by a single agent, or the sum of the therapeutic effects elicited by the single agents of a given combination, or at least 20%, or at least 30%, or at least 40%, or at least 50%, or at least 60%, or at least 70%, or at least 80%, or at least 90%, or at least 100%, or more. A synergistic effect is also an effect that permits reduced dosing of therapeutic agents when they are used in combination.

For example, for the treatment of Pompe disease, a β2 agonist can be administered to a patient in combination with one or more additional therapeutic agents, such as a lysosomal enzyme. Aβ2 agonist and lysosomal enzyme can be components of separate pharmaceutical compositions that are mixed together before administration, or that are administered separately. A β2 agonist can also be administered simultaneously, without mixing (e.g., by delivery of the β2 agonist on an intravenous line by which the lysosomal enzyme is also administered). In other examples, a β2 agonist can be administered separately (e.g., not admixed), but within a short time frame (e.g., within 24 hours) prior to or subsequent to administration of a lysosomal enzyme. In other examples, a β2 agonist can be administered separately (e.g., not admixed), and without any prior, concurrent, or subsequent administration of a lysosomal enzyme. A synergistic effect may support reduced dosing of ERT when used with a β2 agonist.

A lysosomal enzyme can be administered in a form that targets tissues such as the tissues affected by the disease (e.g., heart, muscle, brain). A lysosomal enzyme is optionally administered in conjunction with other agents, such as antihistamines or immunosuppressants or other immunotherapeutic agents that counteract anti-lysosomal enzyme antibodies. Useful lysosomal enzymes include human, recombinant, wild-type or synthetic. Representative lysosomal enzymes for enzyme replacement therapy include glucocerebrosidase (for the treatment of Gaucher disease; U.S. Pat. No. 5,879,680 and U.S. Pat. No. 5,236,838, alpha-glucosidase (e.g., acid alpha-glucosidase) (for the treatment of Pompe disease; PCT International Publication No. WO 00/12740), alpha-galactosidase (e.g., alpha-gal, alpha-galactosidase or alpha-gal) (for the treatment of Fabry Disease; U.S. Pat. No. 5,401,650), alpha-n-acetylgalactosaminidase (for the treatment of Schindler Disease; U.S. Pat. No. 5,382,524), acid sphingomyelinase (for the treatment of Niemann-Pick disease; U.S. Pat. No. 5,686,240) and alpha-iduronidase for the treatment of Hurler, Scheie, or Hurler-Scheie disease (PCT International Publication No. WO 93/10244A1). For gene therapy, genes encoding the aforesaid lysosomal enzymes are described in the preceding patent publications as well. The patents and published patent applications mentioned in this paragraph are specifically incorporated herein by reference in their entirety, and in particular, the disclosures contained therein with respect to the indicated enzymes, and sequences encoding such enzymes, are also incorporated by reference.

The present disclosure also encompasses administration of a functional equivalent of a lysosomal enzyme, i.e., a lysosomal enzyme refers to a compound different from the lysosomal enzyme that, when administered to the patient, replaces the function of the lysosomal enzyme to treat the lysosomal storage disorder. These functional equivalents include mutants, analogs and derivatives of lysosomal enzymes.

For the treatment of Pompe disease, the relevant lysosomal enzyme is acid alpha-glucosidase. One example is a precursor form of human acid alpha-glucosidase, such as recombinant human acid alpha-glucosidase produced in Chinese hamster ovary (CHO) cell cultures (see e.g., Fuller et al., *Eur. J. Biochem.*, 1995, 234:903-909; Van Hove et al., *Proc. Natl. Acad. Sci. USA*, 1996, 93:65-70, the entire teachings of these references are incorporated herein by reference). As another example, for the treatment of Gaucher disease, the relevant lysosomal enzyme is glucocerebrosidase, modified glucocerebrosidase or CEREZYME® enzyme.

The methods of the present disclosure contemplate single as well as multiple administrations, given either simultaneously or over an extended period of time. A therapeutic agent that increases expression of receptors for a lysosomal enzyme can be administered at regular intervals (i.e., periodically) and on an ongoing basis, depending on the nature and extent of effects of the lysosomal storage disease, and also depending on the outcomes of the treatment. For example, periodic administrations may be bimonthly, monthly, biweekly, weekly, twice weekly, daily, twice a day or three times or more often a day. Administrative intervals may also be varied, depending on the needs of the patient. For example, in times of physical illness or stress, if anti-lysosomal enzyme antibodies become present or increase, or if disease symptoms worsen, the interval between doses can be decreased. Therapeutic regimens also take into account half-live of the administered agents.

For example, for the treatment of late-onset GSD II, a therapeutic agent capable of increasing expression of CI-MPR may be administered as a single dose at a single time point, or administered to the patient over the span a several hours (e.g., once every hour, once every two hours, once every three hours, etc.) or over the span of several days (e.g., once a day, once every two days, once every three days, etc.).

Where a combination therapy is used, administration of a therapeutic agent capable of increasing expression of a receptor for a lysosomal enzyme and a lysosomal enzyme can take place once every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or at least once every 1, 2, 3, 4, 5, 6, 7, 8, 9, 10, 11, 12, 13, 14, 15, 16, 17, 18, 19 or 20 weeks, or any combination thereof, using single or divided doses of every 60, 48, 36, 24, 12, 8, 6, 4, or 2 hours, or any combination thereof. For example, for treatment of Pompe disease, the lysosomal enzyme, functional equivalent thereof or gene is administered once every one-two, two-three, three-four or four-five weeks. The therapeutic agent capable of increasing expression of a receptor for a lysosomal enzyme can be administered before, during or after the onset of skeletal complications or pathology.

As another example, a therapeutic agent capable of increasing expression of a receptor for a lysosomal enzyme can be administered prior to, or concurrently with, or shortly thereafter, a lysosomal enzyme, functional equivalent thereof or gene encoding such enzyme. A therapeutic agent capable of increasing expression of a receptor for a lysosomal enzyme may be administered sufficiently prior to administration of the enzyme so as to permit modulation (e.g., up-regulation) of the target cell surface receptors to occur, for example, at least two-three, three-four or four-five days before the lysosomal enzyme is administered. In the case of Pompe disease, a β2 agonist can be administered to a patient about 0.25, 0.5, 1, 2, 3, 4, 5, 6, 7, 8, 9, 10, 11 or 12 hours, or 1, 2, 3, 4, 5, 6, 7, 8 days, prior to administration of acid alpha-glucosidase enzyme, modified acid alpha-glucosidase or a functional equivalent thereof.

A therapeutic agent capable of increasing expression of receptors for a lysosomal enzyme, a lysosomal enzyme, a functional equivalent of a lysosomal enzyme, or a gene encoding a lysosomal enzyme can be administered in a dosage of, for example, 0.1 to 100 mg/kg, such as 0.5, 1.0, 1.1, 1.6, 2, 8, 9, 10, 11, 15, 16, 17, 18, 19, 20, 21, 22, 27, 28, 29, 30, 40, 45, 50, 60, 70, 80, 90 or 100 mg/kg per day. Dosage forms suitable for internal administration generally contain from about 0.1-500 milligrams of active ingredient per unit. In these pharmaceutical compositions the active ingredient is ordinarily be present in an amount of about 0.5-95% by weight based on the total weight of the composition.

As known by those of skill in the art, the optimal dosage of therapeutic agents useful in the invention depend on the age, weight, general health, gender, and severity of the lysosomal storage disease of the individual being treated, as well as route of administration and formulation. A skilled practitioner is able to determine the optimal dose for a particular individual. Additionally, in vitro or in vivo assays may be employed to help to identify optimal dosage ranges, for example, by extrapolation from dose-response curves derived from in vitro or animal model test systems.

The following examples have been included to illustrate modes of the invention. Certain aspects of the following examples are described in terms of techniques and procedures found or contemplated by the present co-inventors to work well in the practice of the invention. In light of the present disclosure and the general level of skill in the art, those of skill appreciate that the following examples are intended to be exemplary only and that numerous changes, modifications, and alterations may be employed without departing from the scope of the invention.

EXAMPLES

Example 1

Generation and Characterization of Murine Models of GAA Deficiency

CI-MPR-KO mice were generated using a muscle-specific promoter (muscle creatine kinase; CK) and the cre/loxP conditional knock out system essentially as described previously (Wylie et al., *Am. J. Pathol.*, 2003, 162: 321-328). The muscle-specific CI-MPR-KO mice were crossed with GAA- KO mice to generate muscle specific DKO mice). This mouse colony was subsequently screened to be GAA−/−, M6PR flox/flox and MCK-Cre positive. These DKO mice and age matched Pompe mice were administered four weekly doses of 20 or 100 mg/kg rhGAA and sacrificed 3 days after the last injection. Selected tissues were collected for GAA enzyme activity levels, glycogen content depletion and Western blot analysis. Pompe and DKO mice injected with vehicle were used as controls.

GAA-KO genotyping was done with a PCR-based assay to determine the deletion of exon 6 in GAA-KO mice. Genomic mouse DNA (100 ng) was used as template in a PCR reaction (35 cycles of 95° C. for 30 seconds, 60° C. for 30 seconds, and 72° C. for 1 minute) using gene-specific primers. This genotyping was carried out till GAA knock out mice colony was successfully established.

Mouse CI-MPR Genotyping was done with a PCR-based assay to determine the presence of the loxP site in M6P/IGF2R intron 9. 100 ng of mouse genomic DNA was used as template in a PCR reaction (35 cycles of 95° C. for 30 seconds, 60° C. for 30 seconds, and 72° C. for 1 minute) using gene-specific primers. Routine genotyping of this colony was needed until the muscle-CI-MPR-KO mouse colony was successfully established.

Mouse Cre genotyping was done with a PCR-based assay was used to determine the presence of Cre recombinase expressed in a specific tissue. Every DKO colony litter was genotyped using 100 ng of mouse genomic DNA as template in a PCR reaction (35 cycles of 95° C. for 30 seconds, 60° C. for 30 seconds, and 72° C. for 1 minute) using gene-specific primers. Mouse tested positive for MCK-Cre were used for experimentation.

Example 2

Preparation of AAV Vectors for ERT in Murine Models of GAA Deficiency 293 cells were transfected with an AAV vector, the AAV packaging plasmid (Gao, G. P. et al. 2002) (courtesy of Dr. James M. Wilson, University of Pennsylvania, Philadelphia, Pa.), and pAdHelper (Stratagene, La Jolla, Calif.). Cell lysate was harvested 48 hours following infection, freeze-thawed 3 times, and isolated by sucrose cushion pelleting followed by 2 cesium chloride gradient centrifugation steps. AAV stocks were dialyzed against 3 changes of Hanks buffer, and aliquots were stored at −80° C. The number of vector DNA containing-particles was determined by DNAse I digestion, DNA extraction, and Southern blot analysis. All viral vector stocks were handled according to Biohazard Safety Level 2 guidelines published by the NIH.

For in vivo analysis of AAV vectors, stocks were administered intravenously (via the retroorbital sinus) in 3 month-old and 15 month-old GAA-KO mice, and to 3 month-old tolerant GAA-KO and DKO mice. Clenbuterol (30 μg/ml) was administered to groups of 3 month-old vector-injected and mock-injected male GAA-KO mice in drinking water for 28 days. At the indicated time points post-injection, tissue samples were obtained and processed as described below. All animal procedures were done in accordance with Duke University Institutional Animal Care and Use Committee-approved guidelines. GAA activity and glycogen content were analyzed essentially as described (Sun et al., *Mol. Ther.*, 2005, 11:889-898; Sun et al., *Mol. Ther.*, 2005, 11: 57-65). Rotarod testing was performed essentially as described (Sun, B. D. et al. 2005). Western blotting of hGAA was performed essentially as described (Amalfitano et al., *Proc. Natl. Acad. Sci. USA,* 1999, 96: 8861-8866) using the hGAA monoclonal antibody (courtesy of Genzyme Corp., Framingham, Mass.) and the CI-MPR antibody (catalog number GTX28093; Gene Tex, Irvine, Calif.).

When comparing animals receiving treatments with controls, groups were assessed by a homoscedastic Student T-test. The significance of differences between multiple groups was tested using a two-sided Wilcoxon rank sum test for continuous variables, and was conducted with Stata 10 (StataCorp LLC, College Station, Tex.). A p-value <0.05 was considered to be statistically significant.

Example 3

Effects of CI-MRP in GAA Uptake and Glycogen Clearance

To further understand the role of CI-MPR in recombinant human GAA (rhGAA) uptake and glycogen clearance specifically in Pompe disease, muscle-specific CI-MPR-KO mice were crossed with GAA-KO (Pompe disease) mice. The DKO mice were administered four weekly doses of 20 mg/kg and 100 mg/kg body weight of recombinant human rhGAA and sacrificed three days after the last injection to evaluate GAA enzyme levels and glycogen depletion in the target tissues. Enzyme activity demonstrated significantly decreased uptake in skeletal tissues (quadriceps, triceps, gastrocnemius) of DKO mice as compared with GAA-KO mice (FIG. 1A). Table 1 presents the differences in GAA uptake and glycogen content between GAA-KO and DKO mice. GAA activity was significantly reduced in the muscle of DKO mice, in comparison with GAA-KO mice. As expected, glycogen content was significantly increased in the muscle of DKO mice, in comparison with GAA-KO mice. A similar decrease was observed in the heart, with 50% reduced rhGAA uptake in the DKO mice as compared with Pompe mice following administration of 100 mg/kg rhGAA.

TABLE 1

Comparison of rhGAA administration in DKO and GAA-KO mice

| Muscle | GAA decrease in DKO v. GAA-KO (%) | GAA (p, DKO v. GAA-KO) | Glycogen increase in DKO v. GAA-KO (%) | Glycogen (p, DKO v. GAA-KO) |
|---|---|---|---|---|
| Heart | 47 | 0.02 | 1600 | 0.04 |
| Diaphragm | 2 | 1 | 192 | 0.06 |
| Quadriceps | 79 | 0.02 | 300 | 0.000001 |
| Triceps | 76 | 0.009 | 425 | 0.0000003 |
| Gastrocnemius | 72 | 0.001 | 340 | 0.000005 |

Figure 1B:
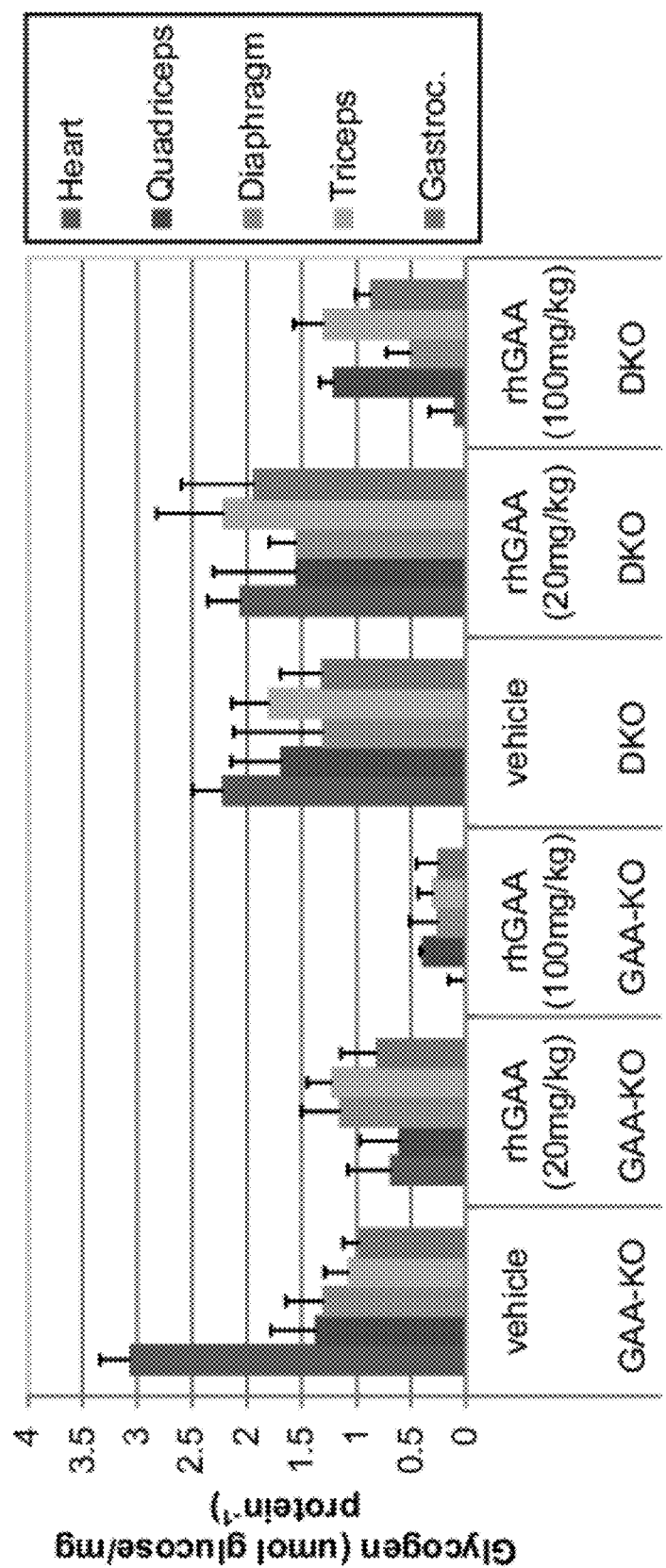

Glycogen content data indicated clear differences in the glycogen clearance observed in the heart of DKO mice as compared to Pompe mice (7% compared to 77% respectively) at the lower dose of rhGAA (20 mg/kg; FIG. 1B and Table 1). However, similar glycogen clearance was observed in DKO and GAA-KO mouse heart tissue following administration of 100 mg/kg rhGAA (95% and 99% respectively). Therefore, skeletal muscle (quadriceps, triceps, gastrocnemius) was largely dependent on CI-MPR for rhGAA enzyme uptake and glycogen clearance in vivo, whereas heart and diaphragm might employ an alternative receptor for enzyme uptake and glycogen depletion besides CI-MPR. In the skeletal muscles, glycogen was increased in the DKO mice as compared with GAA-KO mice even following administration of high dose rhGAA (Table 1; 100 mg/kg). A similar increase was observed in the quadriceps of DKO mice at the lower dose, with only 8% glycogen depletion detected in the DKO mice compared with 55% depletion in GAA-KO mice (Table 1; 20 mg/kg).

The basis for resistance to ERT in DKO mice was further analyzed by Western blot analysis of heart and skeletal muscle, which revealed more than 90% reduction of CI-MPR in DKO mouse, as compared with GAA-KO mice. In skeletal tissue (quadriceps) DKO mice had 40% decreased CI-MPR expression as compared with GAA-KO mice (FIG. 2). These data revealed that CI-MPR expression was reduced, but not completely eliminated in striated muscle of DKO mice. Moreover, the responsiveness of the heart to high dose ERT in DKO mice implicated an alternative, unidentified receptor in the uptake of GAA.

Figure 3A:
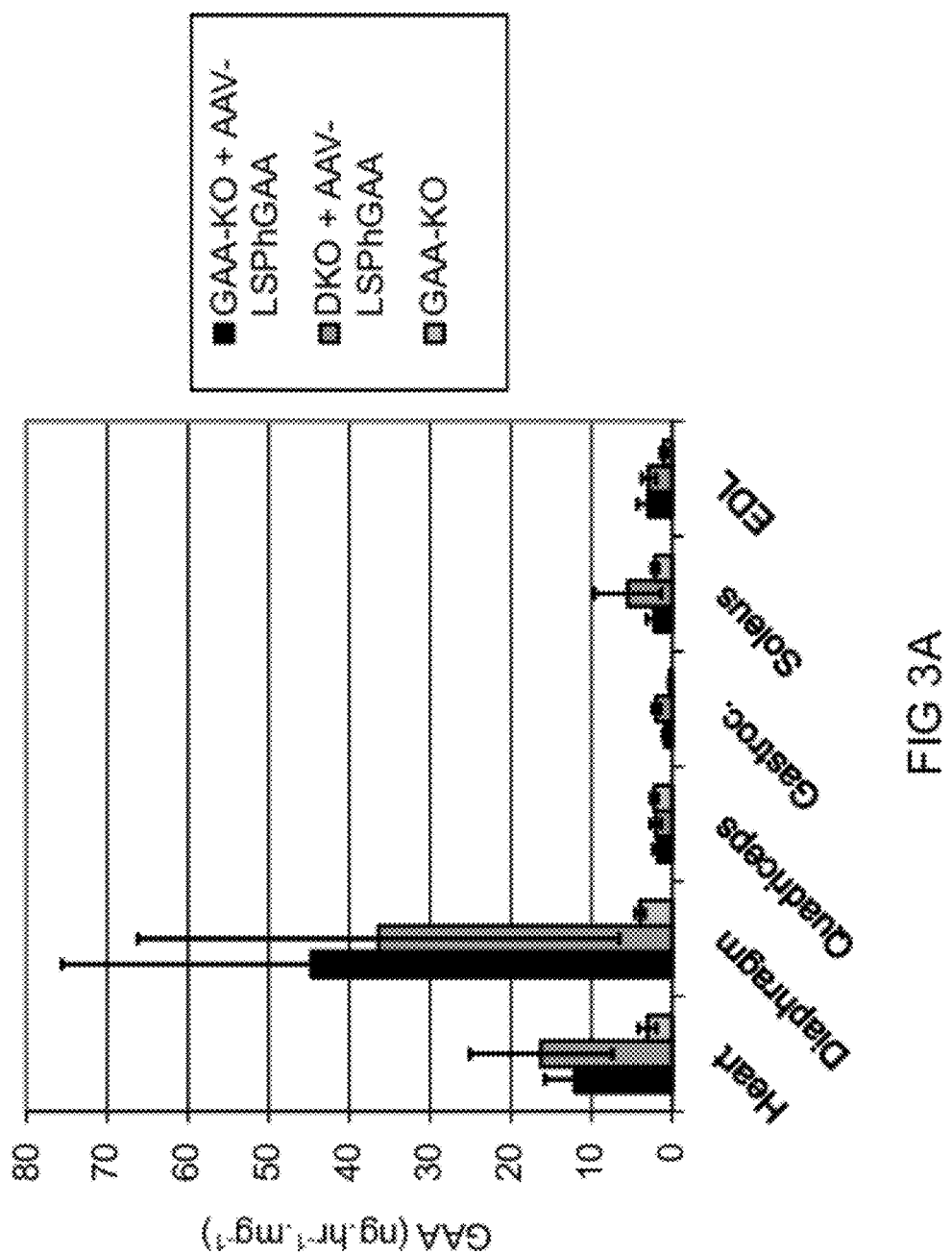
FIG. 3A-3B depicts the impaired liver-targeted gene therapy in DKO mice. The homozygous DKO mice (n=5) and GAA-KO mice (n=4) were injected with a liver-specific regulatory cassette (AAV-LSPhGAA) ($2 \times 10^{10}$ vector particles/mouse) to evaluate the relative effect of MPR depletion upon GAA uptake. Mice were euthanized for tissue analysis 18 weeks after vector injection.
Figure 3B:
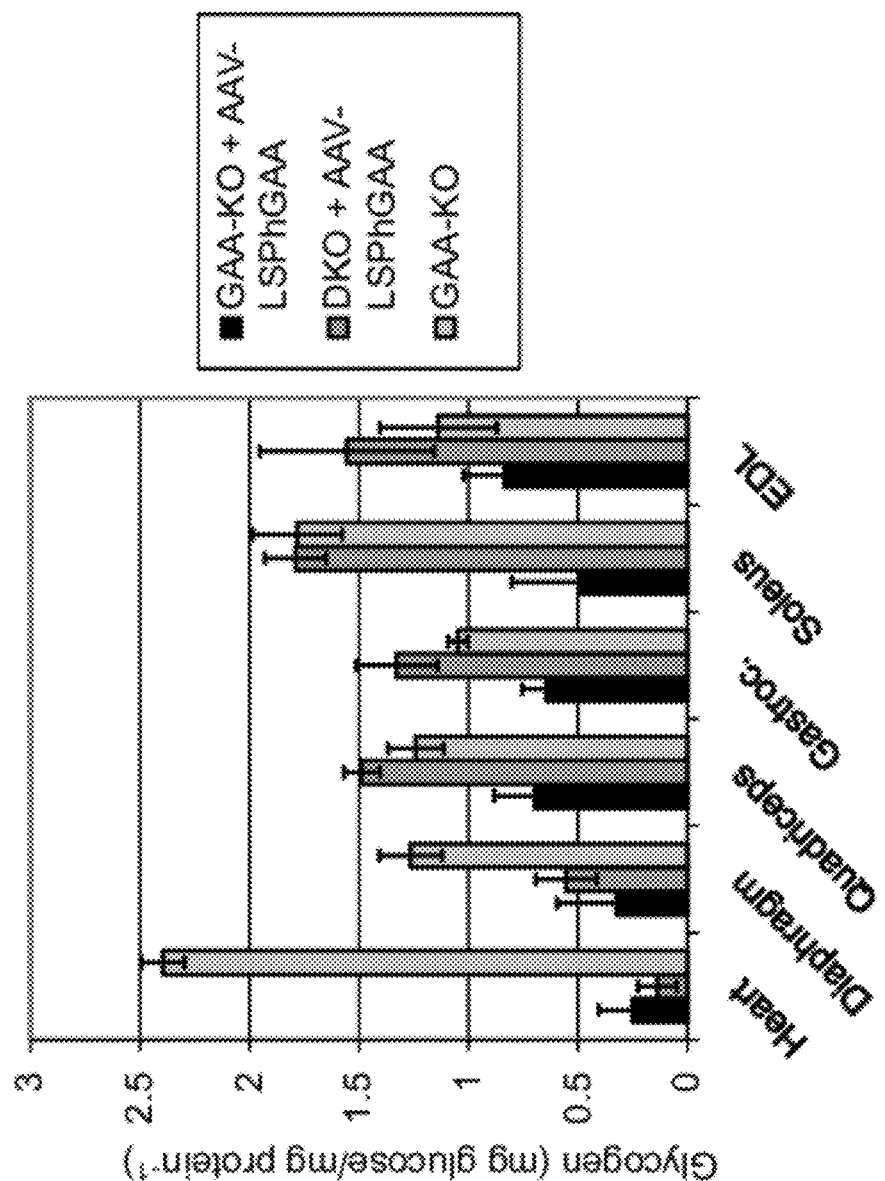

Example 4
Enhanced Efficacy from Liver-Targeted Gene Therapy Plus Clenbuterol Treatment ERT in Pompe disease requires intermittent infusions of rhGAA to correct glycogen storage in striated muscle via receptor-mediated uptake. An analogous gene therapy strategy has been developed, whereby the liver is highly transduced with a recombinant viral vector encoding GAA that creates a depot for the continuous secretion of GAA into the bloodstream (Amalfitano et al., *Proc. Natl. Acad. Sci. USA*, 1999, 96: 8861-8866; Cresawn et al., *Hum. Gene Ther.*, 2005, 16: 68-80). This depot strategy was studied by evaluating an adeno-associated virus (AAV) vector containing a liver-specific regulatory cassette (AAV-LSPhGAA) that had significantly cleared glycogen accumulations from the heart and skeletal muscle of GAA-KO mice (Franco et al., *Mol. Ther.*, 2005, 12: 876-884). The vector particle number administered was reduced to $2 \times 10^{10}$ vector particles/mouse to evaluate the relative effect of CI-MPR depletion upon GAA uptake, given the effects observed in the heart following rhGAA treatment at the lower dose (FIG. 1). Somewhat surprisingly, in contrast with rhGAA treatment no significant differences in GAA activities of muscles were observed following AAV-LSPhGAA administration (FIG. 3A). Given the similar mechanism for GAA uptake into muscle following injection of rhGAA and secretion from the liver, it could be assumed that continuous secretion of GAA from the liver might overcome the deficiency of CI-MPR in the muscle of DKO mice. However, the clearance of glycogen from the skeletal muscle of DKO mice was relatively impaired following administration of AAV-LSPhGAA (FIG. 3B). The glycogen content of diaphragm, gastrocnemius, soleus, and EDL was significantly elevated in DKO mice, in comparison with GAA-KO mice following vector administration (Table 2). The relative lack of glycogen clearance in DKO mice, despite the presence of GAA activity, indicated that intracellular processing and lysosomal targeting was disrupted in absence of CI-MPR expression.

TABLE 2

Comparison of AAV-LSPhGAA administration in DKO and GAA-KO mice

| Muscle | GAA decrease in DKO v. GAA-KO (%) | GAA (p, DKO v. GAA-KO) | Glycogen increase in DKO v. GAA-KO (%) | Glycogen (p, DKO v. GAA-KO) |
|---|---|---|---|---|
| Heart | −35 | 0.4 | 54 | 0.1 |
| Diaphragm | 19 | 0.7 | 170 | 0.03 |
| Quadriceps | −12 | 0.6 | 210 | 0.002 |
| Gastrocnemius | −115 | 0.002 | 210 | 0.0003 |
| Soleus | −148 | 0.1 | 370 | 0.00002 |
| EDL | 3.3 | 0.9 | 190 | 0.008 |

Based upon the implication that CI-MPR expression was crucial to both uptake and intracellular processing of GAA in Pompe disease, levels of CI-MPR in GAA-KO mice were manipulated. A related but distinct strategy for addressing the apparently limiting role of CI-MPR expression in achieving efficacy with ERT in Pompe disease involved enhancement of rhGAA glycosylation (Raben et al., *Mol. Genet. Metab.*, 2003, 80: 159-169; Raben et al., *Transgenic Res.*, 2003, 12: 171-178; McVie-Wylie et al., *Mol. Genet. Metab.*, 2008, 94: 448-455). CI-MPR expression was increased in conjunction with AAV vector administration to demonstrate the dependence of biochemical correction upon receptor-mediated uptake of GAA. The vector-transduced liver depot was enhanced by the addition of a drug, clenbuterol, which increases the expression of CI-MPR in muscle (Matsumoto et al., *Arch. Oral Biol.*, 2006 51:603-611). The liver was transduced by administering AAV-LSPhGAA ($2 \times 10^{10}$ vector particles) to groups of 3 month-old male GAA-KO mice, and clenbuterol (30 μg/ml) was administered to groups of 3 month-old vector-injected and mock-injected male GAA-KO mice in drinking water.

The effect of clenbuterol was evident, when Rotarod testing was performed 4 weeks following vector administration. The Rotarod latency was increased by 75% following vector administration and clenbuterol treatment, in comparison with vector administration alone (FIG. 4A; $p<2 \times 10^{-5}$). Rotarod latency also increased 26% following clenbuterol treatment alone, in comparison with mock treatment ($p=0.02$); whereas vector administration did not increase Rotarod significantly in comparison with mock treatment of GAA-KO mice (FIG. 4A). These data demonstrated a synergistic effect of vector administration and clenbuterol treatment in GAA-KO mice upon motor function. The effect of clenbuterol was further demonstrated by a trend toward greater weight gain following vector administration and clenbuterol treatment, in comparison with mock treatment (FIG. 4B; $p=0.06$).

Figure 5A:
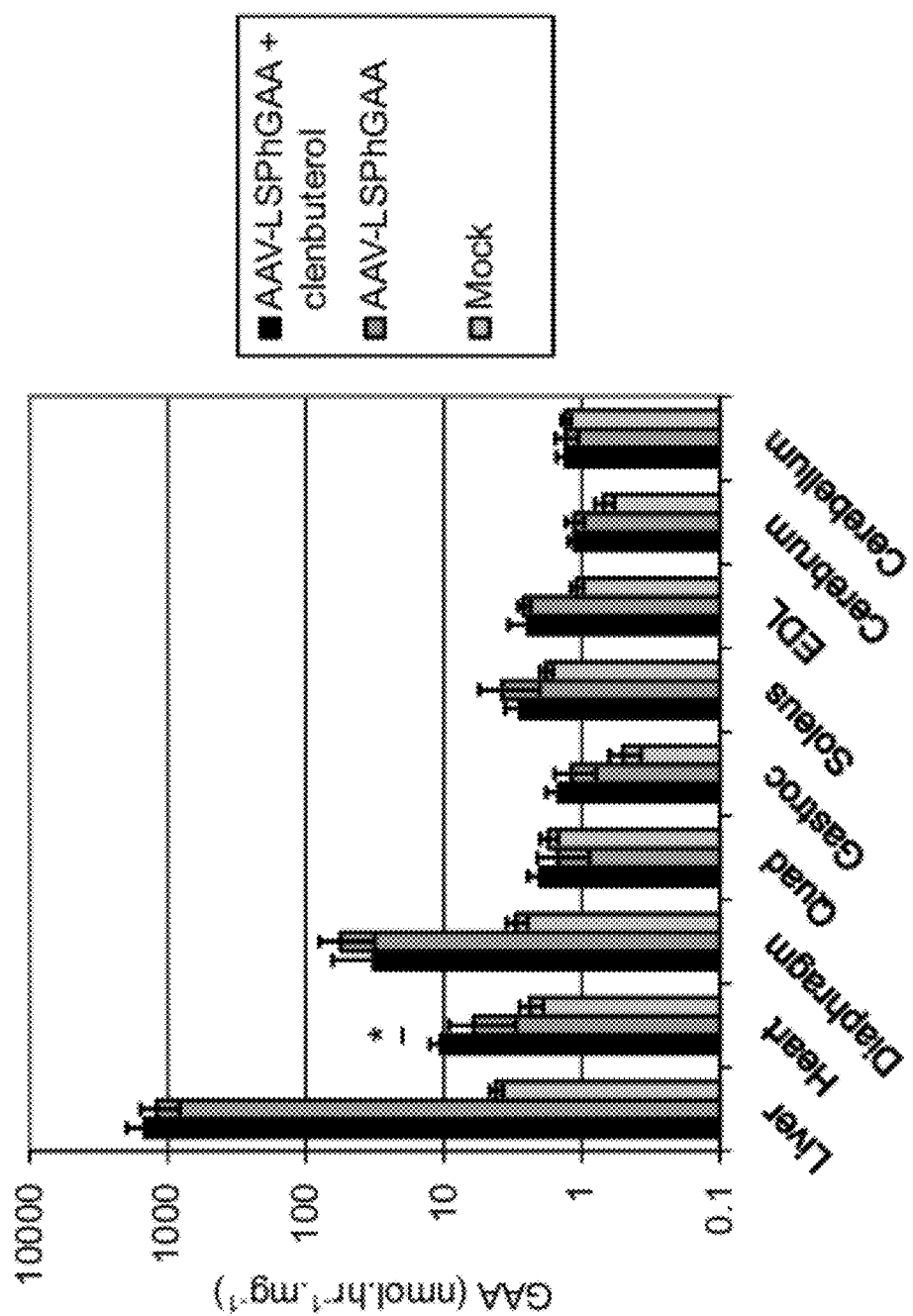
FIG. 5A-5B depicts enhanced efficacy from liver-targeted gene therapy plus clenbuterol treatment. The GAA-KO mice were injected with AAV-LSPhGAA ($2 \times 10^{10}$ vector particles/mouse) or uninjected (5 per group). Vector-treated mice were treated with AAV-LSPhGAA and clenbuterol or with AAV-LSPhGAA alone. Untreated (mock) GAA-KO mice were used as controls. Mice were euthanized for tissue analysis 4 weeks after vector injection.

The efficacy from clenbuterol treatment was evaluated with regard to biochemical correction of GAA deficiency and glycogen storage in striated muscles and the brain. GAA activity was significantly increased in the heart following vector administration and clenbuterol treatment, in comparison with vector administration alone (FIG. 5A; $p=0.03$). GAA activity in skeletal muscles and the brain were significantly increased by clenbuterol administration.

Figure 5B:
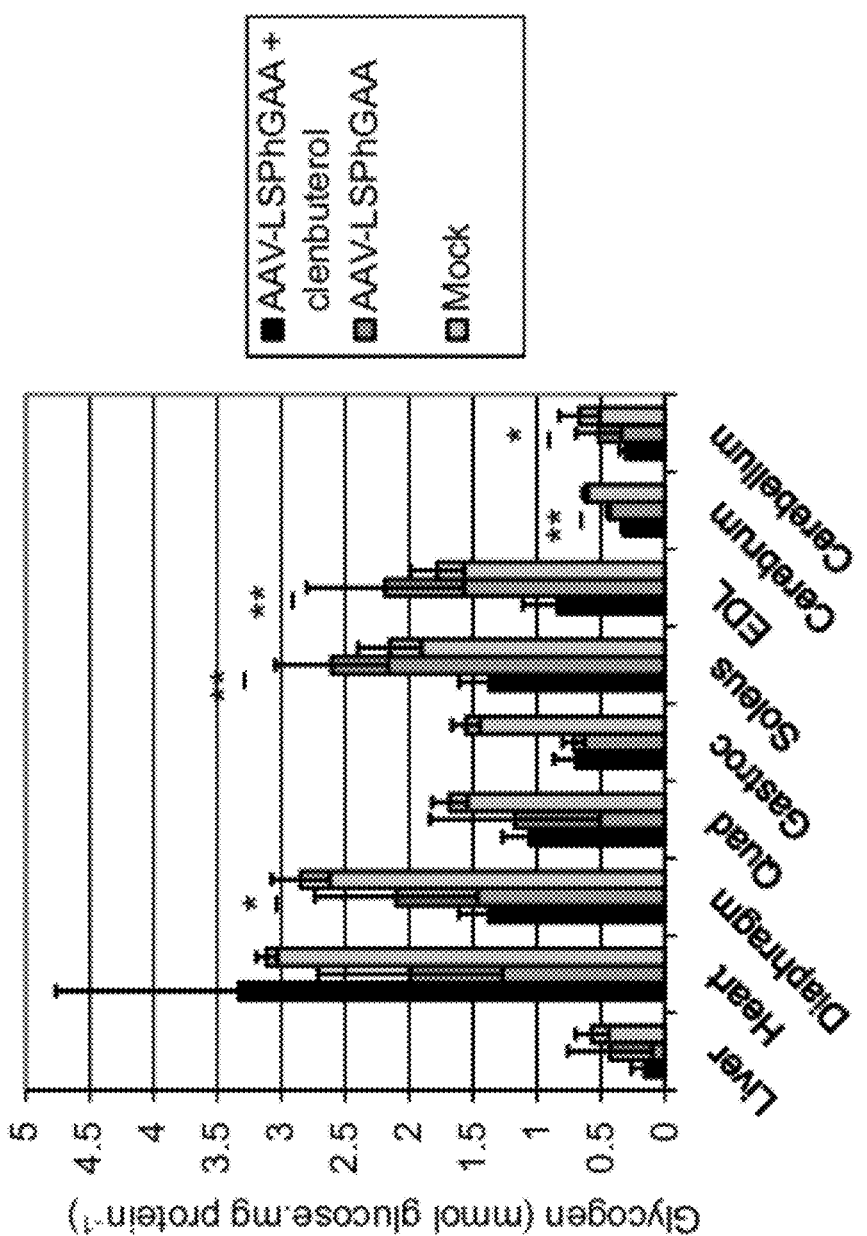

The beneficial effect of clenbuterol administration upon biochemical correction was emphasized by reduced glycogen storage in multiple skeletal muscles and the brain. Glycogen content was reduced in the diaphragm ($p=0.04$), soleus ($p=0.0006$), extensor digitorum longus (EDL; $p=0.002$), cerebrum ($p<5 \times 10^{-5}$), and cerebellum ($p=0.03$) following vector administration and clenbuterol treatment, in comparison with vector administration alone (FIG. 5B).

The upregulation of CI-MPR in the brain was demonstrated by Western blotting detection of CI-MPR. Increased CI-MPR expression was demonstrated in the EDL (FIG. 6A) and cerebrum (FIG. 6B) following clenbuterol administration. Densitometry revealed that the CI-MPR signal was increased in the EDL, cerebrum, and cerebellum following clenbuterol treatment (FIG. 6C). The increased CI-MPR expression correlated with significantly increased GAA activity (FIG. 5A) and decreased glycogen content (FIG. 5B) in the brain following administration of clenbuterol with AAV2/8-LSPhGAA administration.

Example 5

Enhanced Efficacy from ERT Plus Clenbuterol Treatment

Figure 7A:
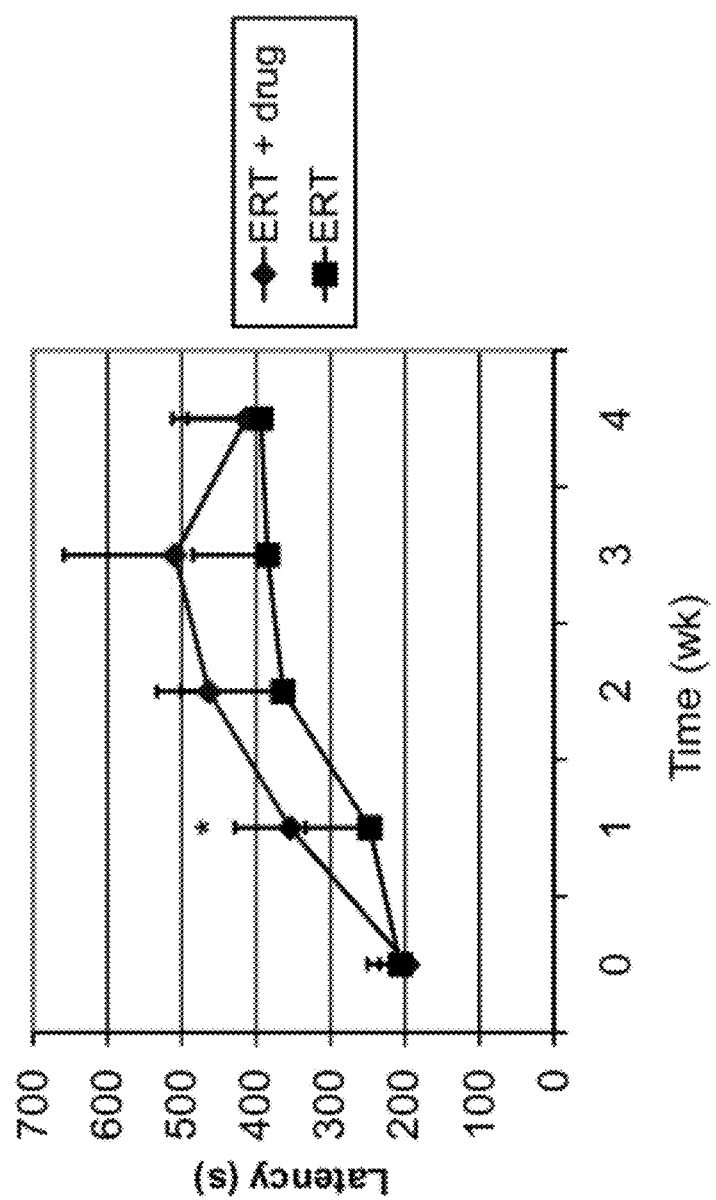
FIG. 7A-7B shows enhanced Rotarod performance and weight gain following ERT plus clenbuterol treatment. GAA-KO mice were administered four weekly doses of rhGAA (20 mg/kg), and treated with clenbuterol (n=5) or ERT alone (n=5).
Figure 7B:
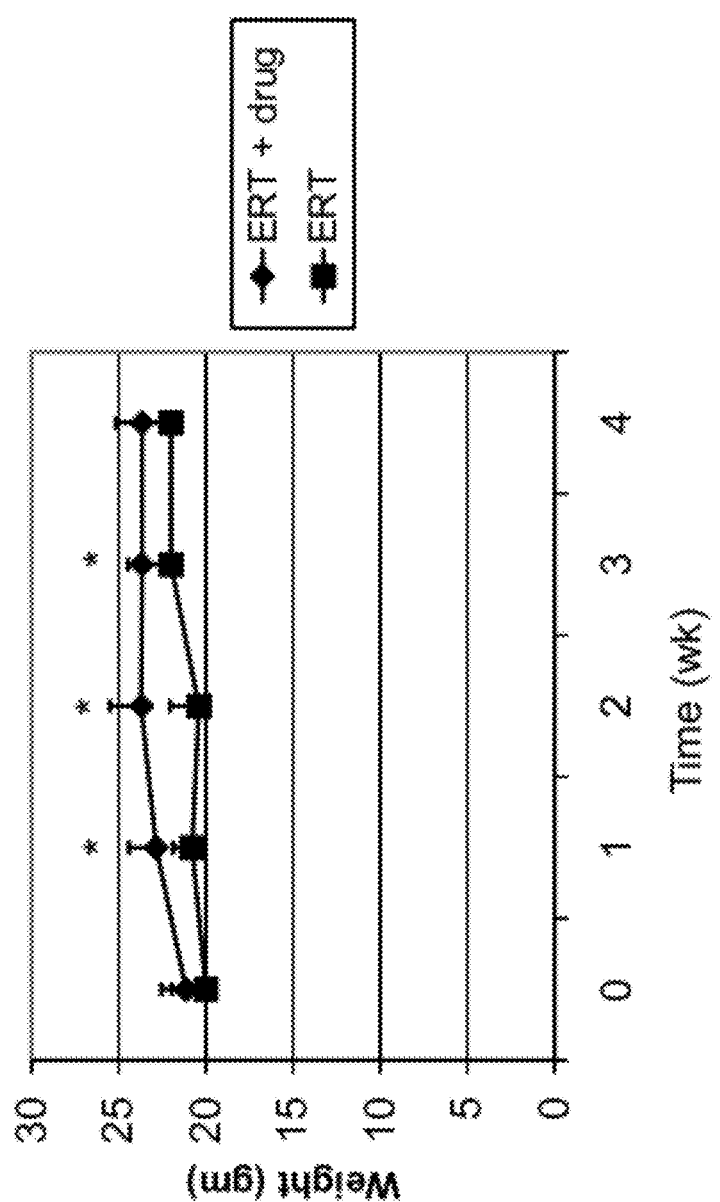

The efficacy from gene therapy was increased by β2 agonist stimulation from clenbuterol treatment, and this benefit might be expected to affect ERT in Pompe disease, as well. Therefore, groups of 3 month-old GAA-KO mice were treated with four weekly doses of rhGAA (20 mg/kg), with or without concurrent clenbuterol treatment. The efficacy of clenbuterol treatment was demonstrated by increased Rotarod latency in groups of male GAA-KO mice (p=0.04 at 1 week), in comparison to male GAA-KO mice treated with ERT alone (FIG. 7A). Furthermore, increased weight gain in male GAA-KO mice treated with clenbuterol supported that muscle hypertrophy was stimulated, in comparison with male GAA-KO mice treated with ERT alone (FIG. 7B; p<0.05 at weeks 1-3).

Figure 8A:
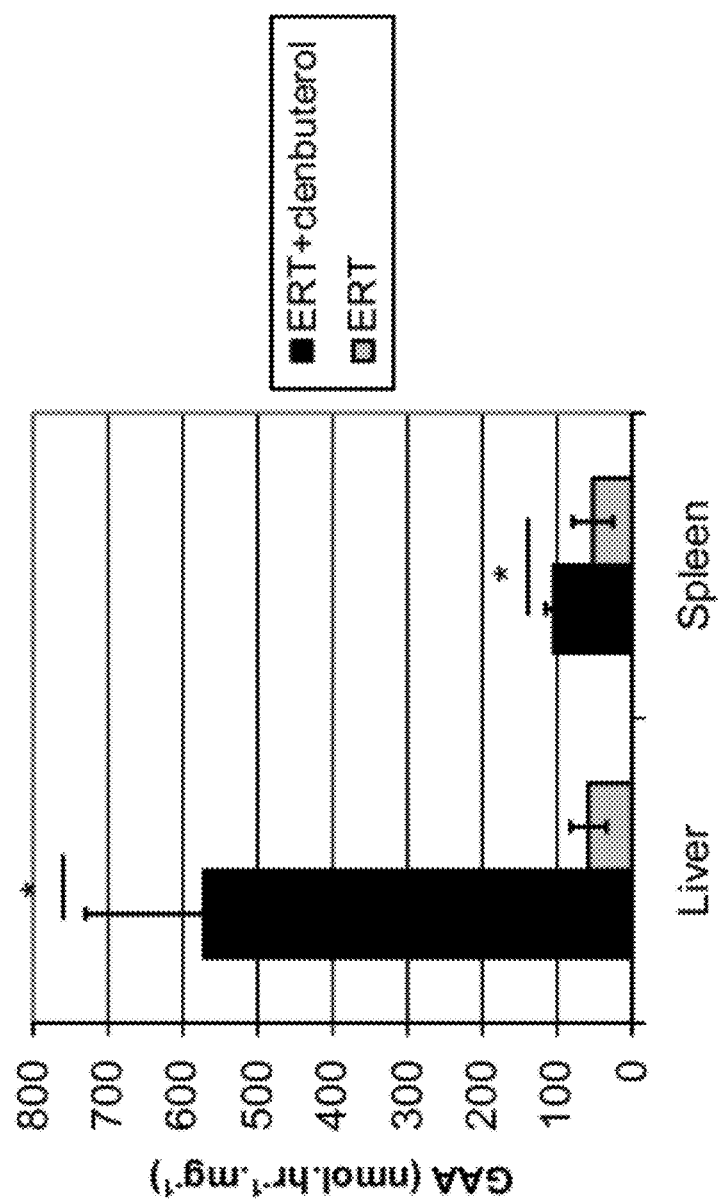
FIG. 8A-8C depicts increased GAA uptake and increased glycogen clearance in GAA-KO mice following clenbuterol treatment and ERT. GAA activity was significantly increased following clenbuterol treatment and ERT in liver, spleen, and gastrocnemius (Gastroc.). Glycogen content was significantly reduced following clenbuterol treatment and ERT in diaphragm, quadriceps, and tibialis anterior (Tib. Ant.). GAA-KO mice were administered four weekly doses of rhGAA (20 mg/kg), and treated with clenbuterol (n=6) or untreated (n=5).
Figure 8B:
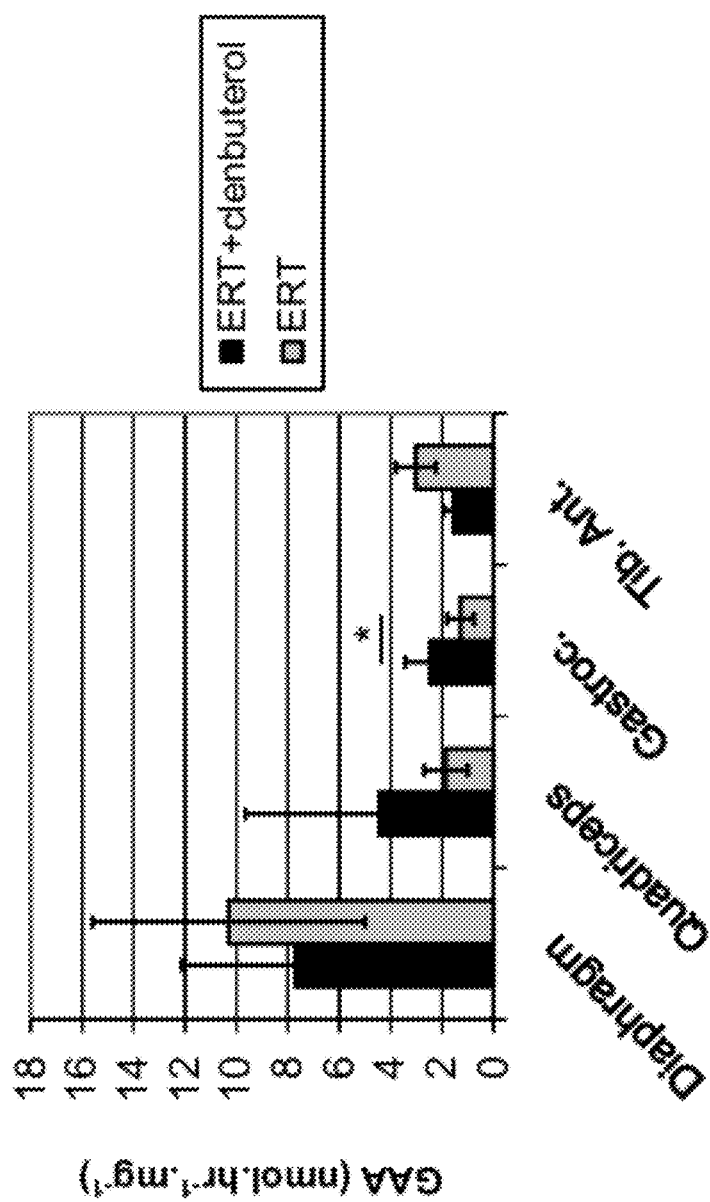
Figure 8C:
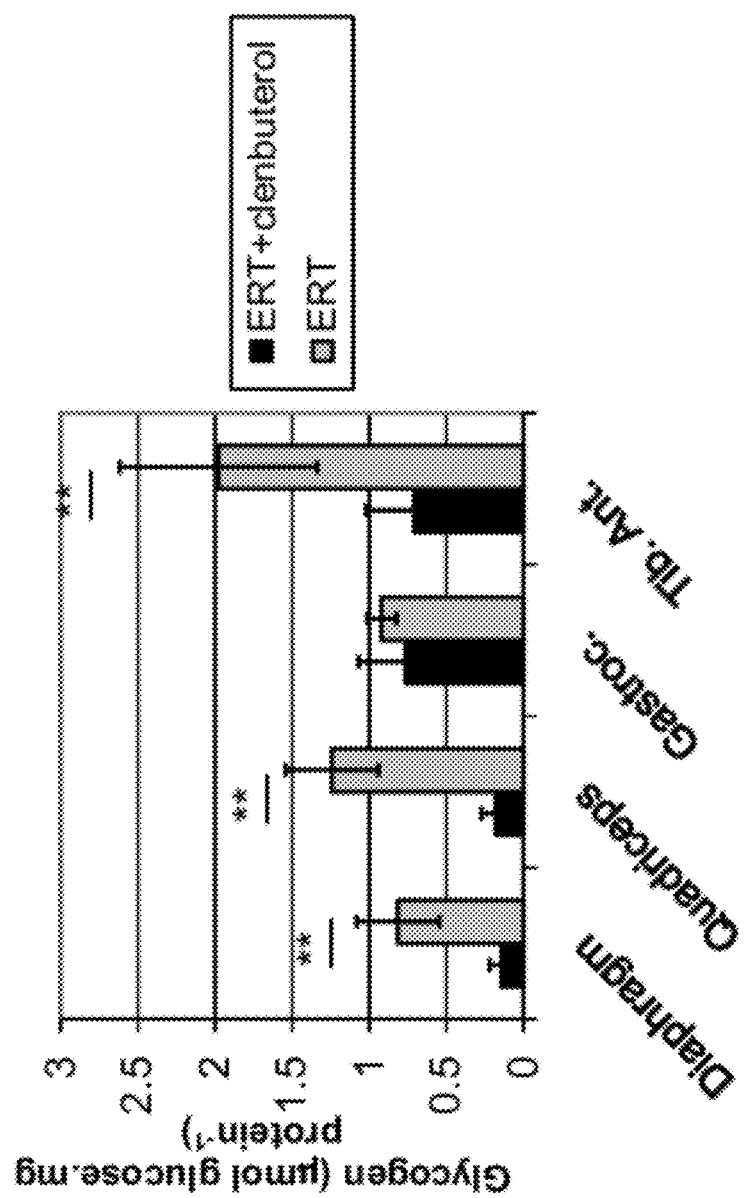

The enhanced efficacy of ERT in conjunction with clenbuterol treatment was further demonstrated by improved biochemical correction of GAA deficiency in both viscera and skeletal muscle. The GAA activity of both liver (p<0.0001) and spleen (p=0.002) was significantly increased in clenbuterol-treated mice following ERT, demonstrating increased uptake of rhGAA by non-muscle tissues (FIG. 8A). The GAA activity for gastrocnemius (p=0.04) was significantly increased for the clenbuterol-treated group, confirming the benefit of CI-MPR upregulation upon the biochemical correction of in skeletal muscle (FIG. 8B). As anticipated, glycogen content was significantly reduced for diaphragm (p=0.0002), quadriceps (p=0.00002), and tibialis anterior (p=0.002) (FIG. 8C). The absence of increased glycogen clearance in the gastrocnemius from clenbuterol treatment, despite significantly increased GAA activity, indicated that other factors might contribute to the reversal of glycogen storage in that muscle.

Figure 9:
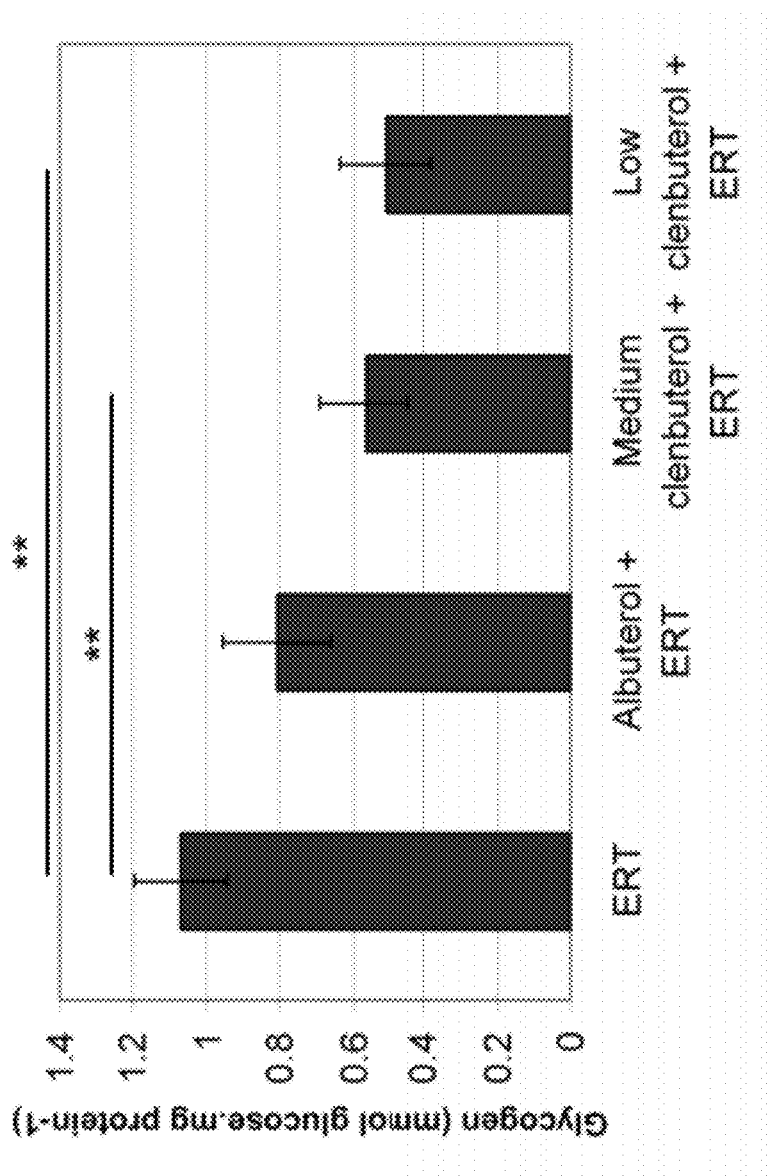
FIG. 9 shows increased glycogen clearance in quadriceps following ERT with clenbuterol or albuterol treatment. GAA-KO mice were treated with weekly rhGAA (20 mg/kg): with medium clenbuterol, 6 mg/ml (n=6), with low clenbuterol, 1.3 mg/ml (n=6), with albuterol 30 mg/ml (n=4), or without drug treatment (n=3). Drugs were administered in the drinking water. Mean+/−s.d. shown. Statistically significant differences indicated (*=p<0.05; **=p<0.01).

The dose of clenbuterol was reduced to investigate efficacy from lower dosages, to reduce side effects that might be encountered. The glycogen content for quadriceps was significantly reduced for 5 and 25-fold reduced dosages of clenbuterol (p<0.001 for clenbuterol 6 μg/ml (Medium) and 1.3 μg/ml (Low) in drinking water), indicating that far lower, better tolerated dosages of clenbuterol would be efficacious in Pompe disease (FIG. 9).

The effects of albuterol were also evaluated. Treatment with albuterol (30 μg/ml drinking water) demonstrated a trend toward decreasing the glycogen content of the quadriceps (FIG. 9). Therefore additional β2 agonists might enhance efficacy during ERT in Pompe disease.

The modulating effect of CI-MPR was confirmed by analyzing the efficacy from GAA replacement therapy in mice with Pompe disease, either when expression was depleted or enhanced. DKO mice featured defective rhGAA uptake in skeletal muscle during ERT, although the uptake of rhGAA by the heart was compensated from the presence of another, unknown receptor. Decreased rhGAA uptake in DKO mice resulted in residual glycogen storage, in comparison with GAA-KO mice treated simultaneously with ERT. An alternative model for biochemical correction of GAA deficiency in the face of CI-MPR depletion was evaluated in the form of liver-transduced DKO mice. Somewhat surprisingly, GAA accumulated to equivalent levels in the skeletal muscle of DKO and GAA-KO mice following AAV vector administration, implying that continuous secretion of GAA from the liver resulted in equivalent uptake of GAA; however, the resistance of glycogen to clearance from the skeletal muscle of DKO mice indicated that intracellular trafficking of GAA to lysosomes was deficient. In addition, the upregulation of CI-MPR by treatment with clenbuterol enhanced the response to both gene therapy and ERT in GAA-KO mice.

Example 6

Enhanced Efficacy from Simultaneous ERT and β2 Agonist Administration

Two β2 agonists were evaluated in combination with ERT, clenbuterol and albuterol. The dose of clenbuterol was reduced 5-fold from the concentration used in Example 4, to 6 mg/l in drinking water, while albuterol was evaluated at the higher dose (30 mg/l in drinking water). Groups of 3 month-old immune tolerant GAA-KO mice (Raben et al., *Human Mol. Genet.*, 2001, 10:2039-2047) were treated with four weekly doses of rhGAA (20 mg/kg body weight), with or without concurrent β2 agonist treatment. Tolerant GAA mice do not form anti-GAA antibodies or develop hypersensitivity reactions during ERT with rhGAA, similar to the majority of patients with Pompe disease (Raben et al., *Mol. Genet. Metab.*, 2003, 80:159-169; Kishnani et al., *Neurology*, 2007, 68:99-109).

Mice were sacrificed 7 days after the last injection. Selected tissues were collected for GAA enzyme activity and glycogen content analyses. All animal procedures were done in accordance with Duke University Institutional Animal Care and Use Committee-approved guidelines. GAA activity and glycogen content analyses, Rotarod testing, and Western blot detection of CI-MPR was performed essentially as described (Koeberl et al., *Mol. Genet. Metab.*, 2011, 103:107-112. Wire hang testing was performed with a 0.5 cm mesh hardware cloth fixed to an 8 by 10 inch frame. Mice were placed on the wire mesh, which was slowly inverted 6 inches over a cage containing paper bedding. The latency, or time until the mouse fell into the cage, was recorded.

Figure 10A:
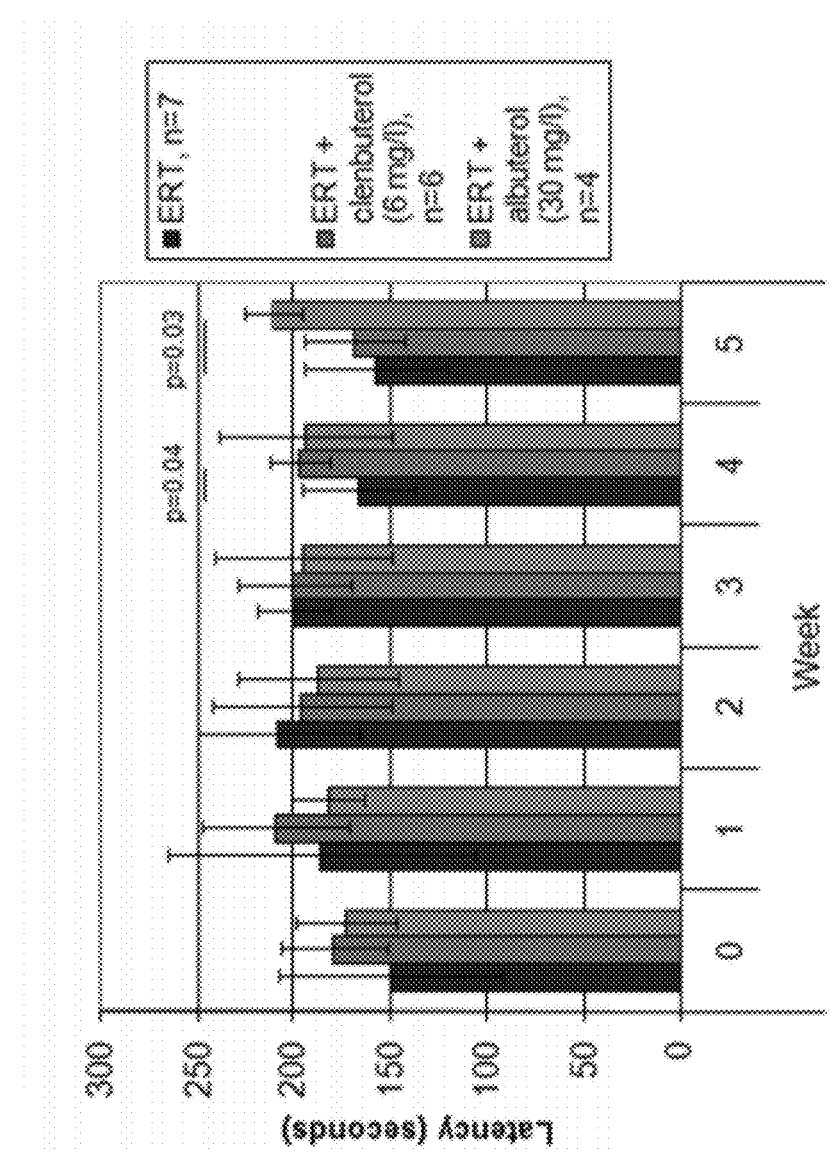
FIG. 10A-10C shows increased Rotarod latency, wire hang latency, and gastrocnemius weight following β2 agonist treatment. GAA-KO mice were administered four weekly doses of rhGAA (20 mg/kg), and treated with medium dose clenbuterol (n=7), albuterol (n=4) or untreated (n=6 or 3).
Figure 10C:
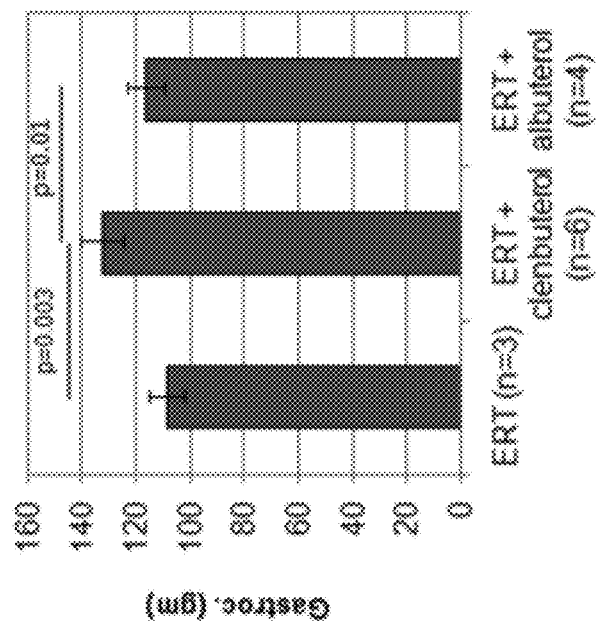
Figure 10B:
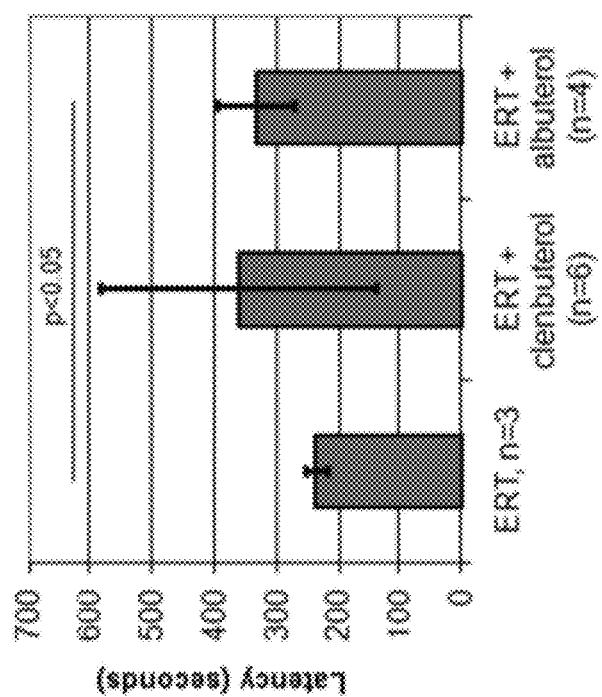

The efficacy of β2 agonist treatment was demonstrated by an increase in Rotarod and wire hang latency. Clenbuterol significantly increased Rotarod latency after 4 weeks of treatment, while albuterol increased latency one week later, in comparison with GAA-KO mice treated with ERT alone (FIG. 10A). Wire hang latency increased significantly following clenbuterol treatment, in comparison with tolerant GAA-KO mice treated with ERT alone (FIG. 10B). The weight of the gastrocnemius increased in mice treated with clenbuterol, in comparison with GAA-KO mice treated with ERT alone or with albuterol plus ERT (FIG. 10C), consistent muscle hypertrophy in response to clenbuterol (Matsumoto et al., *Arch. Oral. Biol.*, 2006, 51:603-611).

Figure 11A:
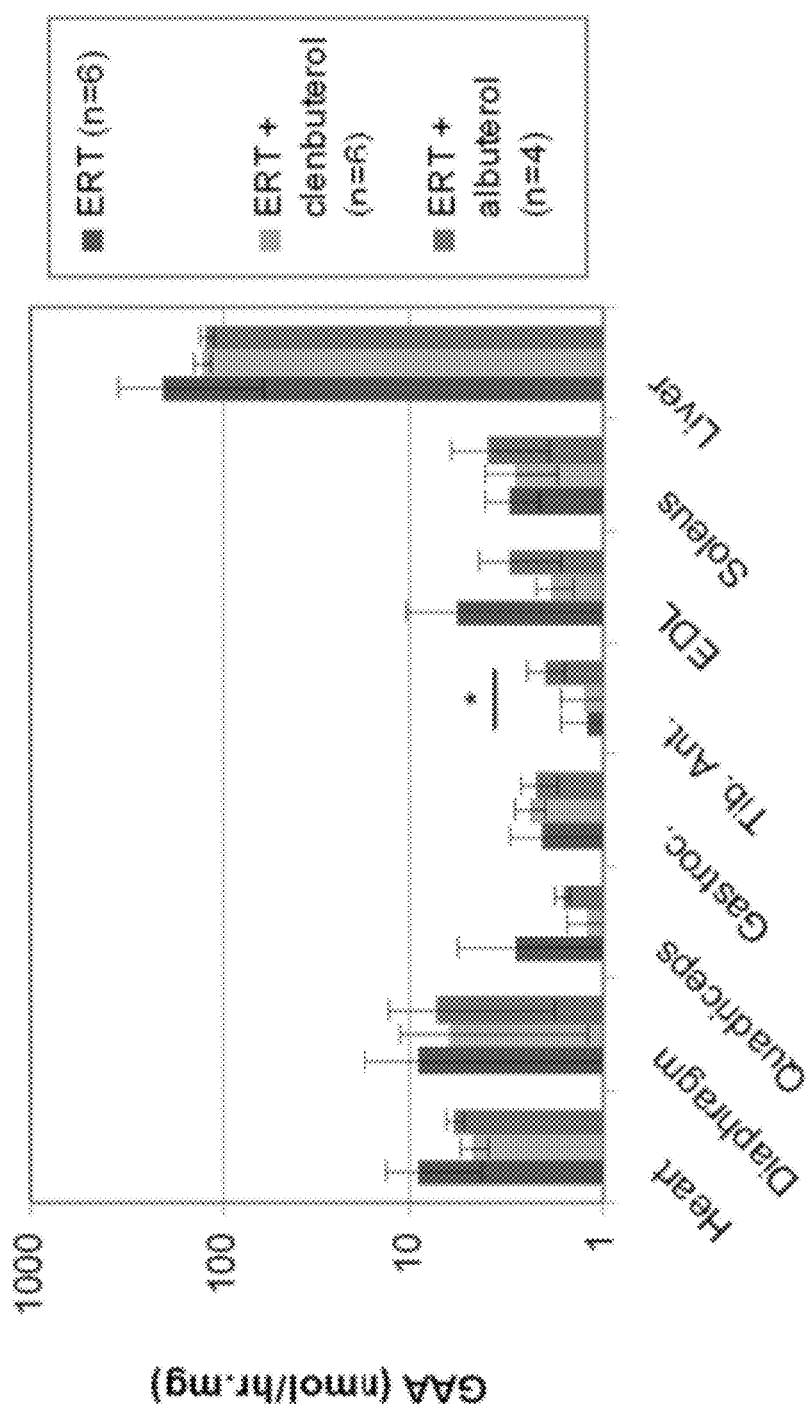
FIG. 11A-11B shows enhanced efficacy following β2 agonist treatment. Male GAA-KO mice were administered four weekly doses of 20 mg/kg body weight of rhGAA and sacrificed one week following the last injection. Groups of mice were treated with clenbuterol (n=6), albuterol (n=4) or untreated (n=6). Mice were euthanized for tissue analysis 5 weeks after initiation of ERT.
Figure 11B:
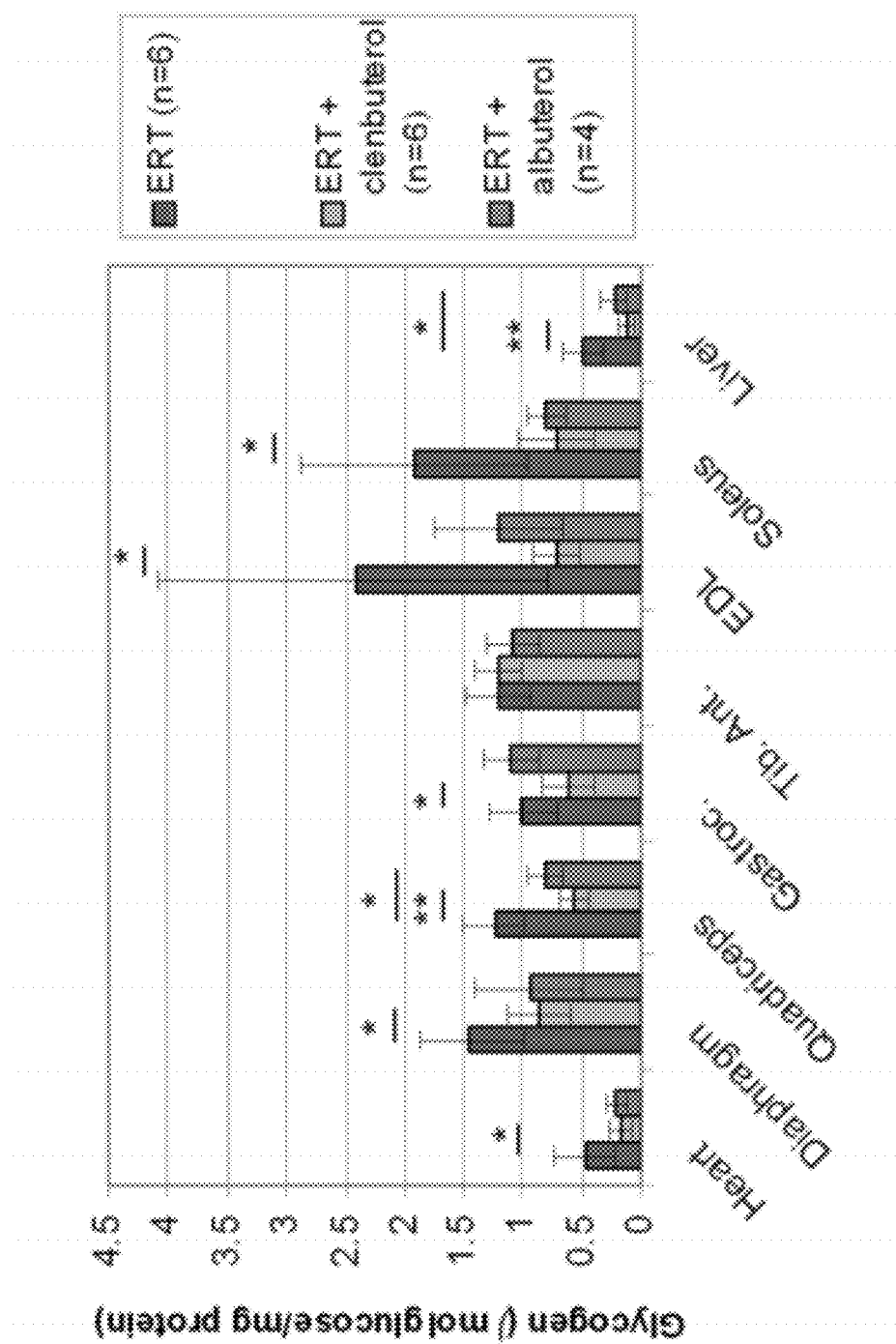

The efficacy of β2 agonist treatment was further demonstrated by an enhanced biochemical correction of striated muscle and the liver. GAA activity was increased only in the tibialis anterior by albuterol treatment, in comparison with ERT alone (FIG. 11A). However, the glycogen content was reduced significantly in all striated muscles with the exception of tibialis anterior by clenbuterol treatment, in comparison with ERT alone (FIG. 11B), despite the lack of increased GAA activity in those tissues (FIG. 11A). Furthermore, albuterol significantly reduced the glycogen content in the quadriceps and liver, in comparison with ERT alone (FIG. 11B), despite the lack of increased GAA activity in those tissues (FIG. 11A). Notably, the quadriceps, gastrocnemius, and extensor digitorum longus (EDL) are skeletal muscles comprised primarily of type II myofibers that have typically resisted the therapeutic effects of ERT in Pompe disease (Raben et al., *Mol. Ther.*, 2005, 11:48-56). The combined data from clenbuterol and albuterol demonstrated that biochemical correction was enhanced despite the unchanged GAA activity in tissues, as reflected by reduced glycogen content following β2 agonist treatment.

Figure 12A:
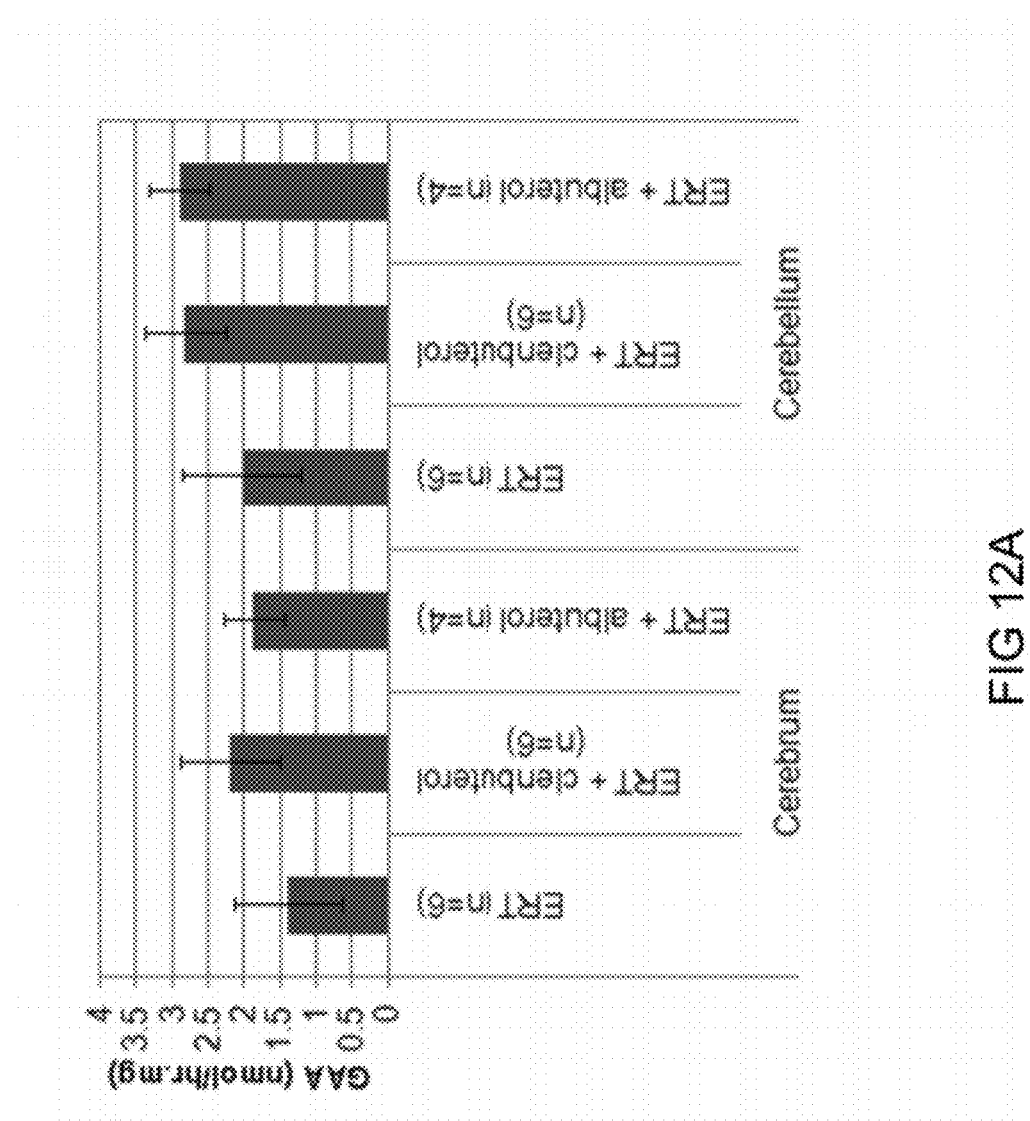
FIG. 12A-12B shows biochemical profile in the cerebellum following β2 agonist administration. Cerebral and cerebellar hemispheres were analyzed 5 weeks following the initiation of ERT. Groups of mice were treated with clenbuterol (n=6), albuterol (n=4) or untreated (n=6).
Figure 12B:
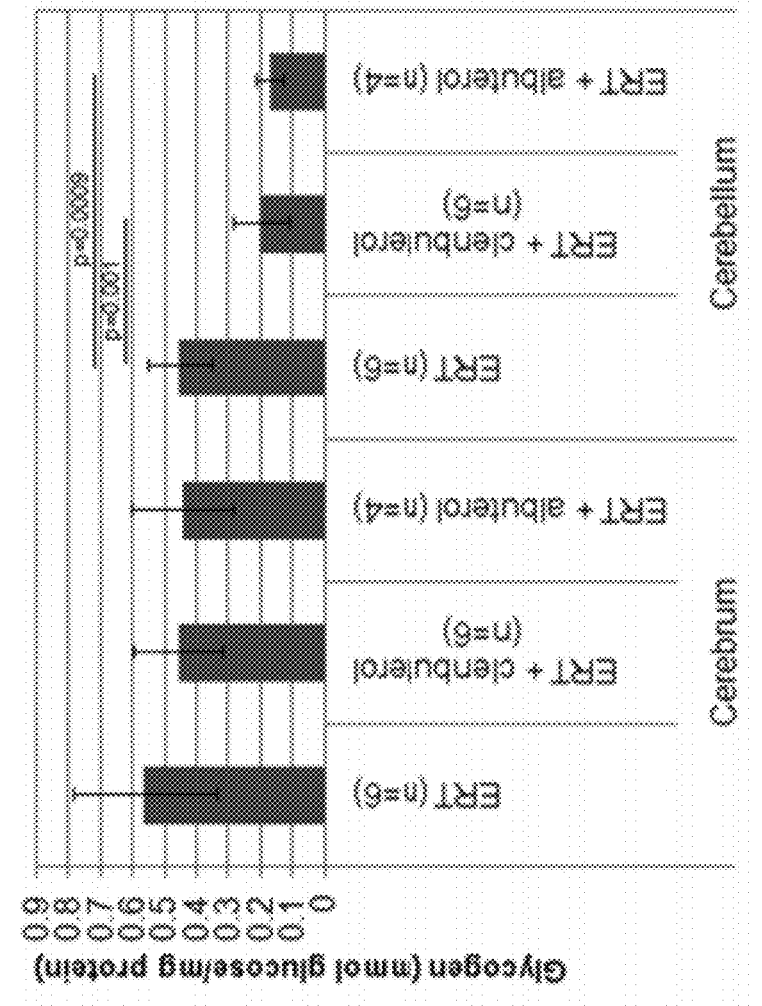

The effect of β2 agonist treatment was further evaluated by biochemical evaluation of the brain. The cerebral and cerebellar hemispheres were analyzed separately, and a trend toward increased GAA activity was demonstrated in the cerebellum following clenbuterol (p=0.08) and albuterol (p=0.09) treatment (FIG. 12A). Glycogen content was reduced significantly by either clenbuterol or albuterol treatment in the cerebellum (FIG. 12B), which is a site of glycogen accumulation in infantile Pompe disease (Thurberg et al., *Lab Invest.*, 2006, 86:1208-1220).

Histopathology was performed to examine brain involvement, and glycogen accumulations were detected in the cerebellum with ERT alone. Albuterol and clenbuterol each reduced the glycogen staining in the cerebellum, in comparison with ERT alone.

Example 7

Administration of β2 Agonist to Patients with Adult-Onset Glycogen Storage Disease The efficacy of clenbuterol treatment in patients with late-onset Pompe disease (LOPD) is evaluated during a 12 week study. Optionally, patients are also undergoing, will undergo, or have completed ERT. Muscle and pulmonary function testing are the primary endpoints. A secondary endpoint is monitored, the urinary Glc4 biomarker, when the subjects are evaluated at baseline, week 4 and week 12. The diagnosis of GSD II is confirmed biochemically using standard fluorimetric techniques using compounds such as α-methyl-umbelliferone-α-glucoside or maltose (see e.g., Angelini et al., *Arch. Neurol.*, 1972, 26:344-349). Subjects with GSD II/LOPD are selected for clenbuterol therapy (40-80 µg per oral daily), either alone or in combination with ERT.

Subjects are monitored daily for 3 days initially for clinical signs of toxicity, following initiation of β2 agonist therapy. The first subjects start a low dose of clenbuterol (40 µg). Subsequently, if no dose-limiting toxicity in the first 3 subjects, these subjects advance to a higher dose (80 µg) after the second day of the 3 day monitoring period. Subjects return for safety and efficacy monitoring after 4 and 12 weeks of clenbuterol therapy.

Muscle strength and muscle function testing is evaluated at Week 0, 4 and 12. A functional grading system for muscle strength is evaluated (Brooke et al., *Muscle & Nerve*, 1983, 6:91-103; Brooke et al., *Arch. Neurol.*, 1987, 44:812-817). Timed functional tests include the GSGC (Moxley III, Muscle & Nerve, 1990, S26-S29), and qualitative scoring of timed test activities including a gait scale (Angelini et al., *Ther. Adv. Neurol. Disord.*, 2009, 2:143-153). The 6 minute walk test is performed (ATS Statement, *Am. J. Respir. Crit. Care Med.*, 2002, 166:111-117). Pulmonary function is assessed in both the supine and upright positions to increase sensitivity for abnormalities detected in Pompe disease (Van Capelle et al., *Neuromuscul. Disord.*, 2010, 20:775-782).

Subjects undergo a muscle biopsy of the quadriceps at the baseline and 12 weeks visit. The muscle biopsy is evaluated for biochemical correction as determined by GAA activity and glycogen content, and for CI-MPR expression by standard methods (Koeberl et al., *Mol. Genet. Metab.*, 2011, 103: 107-112).

What is claimed:

1. A method of treating a patient having a lysosomal storage disease characterized by reduced or deficient activity of a lysosomal enzyme comprising administering a β2 agonist to the patient to thereby increase expression of receptors for the lysosomal enzyme and to decrease lysosomal enzyme metabolite accumulation of the lysosomal storage disease in the patient.

2. The method of claim 1, wherein the β2 agonist is administered prior to or subsequent to a lysosomal enzyme replacement therapy.

3. The method of claim 1, wherein the patient is a human patient.

4. The method of claim 1, wherein the lysosomal storage disease is Pompe disease, adult-onset glycogen storage disease II (GSD II), Gaucher disease, Fabry disease, mucopolysaccharidosis type I, mucopolysaccharidosis type II, or Niemann-Pick disease.

5. The method of claim 1, wherein the lysosomal storage disease is characterized by reduced or deficient activity of the lysosomal enzyme in the brain of the patient.

6. The method of claim 1, wherein the lysosomal enzyme is acid α-glucosidase.

7. The method of claim 1, wherein the receptors are Cation Independent Mannose-6-Phosphate Receptors (CI-MPR).

8. The method of claim 1, wherein the β2 agonist is clenbuterol, formoterol, salmeterol, albuterol, or a combination thereof.

9. The method of claim 1, wherein the administering is performed orally, intranasally, intravenously, intramuscularly, or transdermally.

10. The method of claim 1, wherein expression of receptors for the lysosomal enzyme is increased in the brain of the patient.

11. The method of claim 1, wherein the β2 agonist is administered prior to or subsequent to a gene therapy, wherein the gene therapy comprises expression of a vector encoding a lysosomal enzyme in the patient.

12. The method of claim 11, wherein the vector is a viral vector.

13. The method of claim 12, wherein the viral vector is an adeno-associated virus (AAV) vector.

14. The method of claim 2, wherein the patient receives the lysosomal enzyme replacement therapy prior to increasing expression of receptors for the lysosomal enzyme in the patient.

15. The method of claim 2, wherein the patient receives the lysosomal enzyme replacement therapy subsequent to increasing expression of receptors for the lysosomal enzyme in the patient.

16. The method of claim 1, further comprising administering a lysosomal enzyme replacement therapy to the patient concurrently with the β2 agonist.

17. The method of claim 2, whereby efficacy of the enzyme replacement therapy in brain is enhanced.

* * * * *

UNITED STATES PATENT AND TRADEMARK OFFICE
Certificate

Patent No. 8,679,478 B2                                                                   Patented: March 25, 2014

On petition requesting issuance of a certificate for correction of inventorship pursuant to 35 U.S.C. 256, it has been found that the above identified patent, through error and without any deceptive intent, improperly sets forth the inventorship.
    Accordingly, it is hereby certified that the correct inventorship of this patent is: Dwight D. Koeberl, Durham, NC (US); and Priya S. Kishnani, Durham, NC (US).

Signed and Sealed this Twenty-first Day of October 2014.

*BRANDON FETTEROLF*
*Supervisory Patent Examiner*
Art Unit 1672
Technology Center 1600